(12) United States Patent
Maresca, Jr. et al.

(10) Patent No.: US 9,228,932 B1
(45) Date of Patent: Jan. 5, 2016

(54) METHOD AND APPARATUS FOR EXTENDING THE TIME BETWEEN OUT-OF-SERVICE, IN-TANK INSPECTIONS

(71) Applicant: Vista Precision Solutions, Inc., Richland, WA (US)

(72) Inventors: Joseph W. Maresca, Jr., Sunnyvale, CA (US); Stephen D. Ford, Tipp City, OH (US); Douglas W. Mann, Tipp City, OH (US)

(73) Assignee: Vista Precision Solutions, Inc., Richland, WA (US)

( * ) Notice: Subject to any disclaimer, the term of this patent is extended or adjusted under 35 U.S.C. 154(b) by 237 days.

(21) Appl. No.: 13/786,316

(22) Filed: Mar. 5, 2013

Related U.S. Application Data

(60) Provisional application No. 61/634,786, filed on Mar. 5, 2012.

(51) Int. Cl.
*G06F 19/00* (2011.01)
*G01N 17/00* (2006.01)
*G01N 29/14* (2006.01)

(52) U.S. Cl.
CPC ............... *G01N 17/00* (2013.01); *G01N 29/14* (2013.01)

(58) Field of Classification Search
CPC ... G01M 3/3263; G01M 3/3245; G01M 3/00; F17D 5/06
USPC ............................................. 702/34, 182–185
See application file for complete search history.

(56) References Cited

U.S. PATENT DOCUMENTS

| | | | | |
|---|---|---|---|---|
| 2007/0186623 | A1* | 8/2007 | Wolford | G01M 3/3263 73/49.2 |
| 2010/0212404 | A1* | 8/2010 | Wolford | G01M 3/00 73/45.5 |

* cited by examiner

*Primary Examiner* — Edward Raymond
(74) *Attorney, Agent, or Firm* — David H. Jaffer; Pillsbury Winthrop Shaw Pittman LLP

(57) ABSTRACT

A method and apparatuses to extend the time interval between out-of-service, in-tank inspections while insuring structural integrity using a risk-based, Bayesian statistical approach comprised of a passing leak detection test and the using the results from (1) tank floor thickness measurements, (2) prior out-of-service tank floor inspection results, and/or (3) acoustic emission corrosion maps of the tank floor to estimate the minimum thickness and maximum corrosion rate of the tank during the extension period. The present invention uses an in-tank, mass-based leak detection system to establish tank integrity, three or more ultrasonic (UT) thickness measurement sensors for measurements of the tank floor at one location, and to establish the spatial distribution of corrosion of the tank floor, one or more prior API 653/12R1 or STI SP001 tank floor thickness inspections and/or three or more in-tank AE sensors mounted inside the tank with vertical and horizontal locations in an oblique plane relative to the tank floor.

65 Claims, 6 Drawing Sheets

METHOD AND APPARATUS FOR EXTENDING THE TIME BETWEEN OUT-OF-SERVICE, IN-TANK INSPECTIONS

RELATED APPLICATIONS

This application claims priority to U.S. Provisional Patent Application Ser. No. 61/634,766 filed Mar. 5, 2012, and which is hereby incorporated by reference.

FIELD OF INVENTION

The present invention relates to a method for extending the time between inspections of out-of-service storage tanks for petroleum products and chemicals.

BACKGROUND OF THE INVENTION

There are several standards for inspecting the integrity of welded or riveted, atmospheric pressure, aboveground storage tanks (ASTs) after they have been placed in service. API 653 (API 12R1 is similar to API 653 but is designed for production tanks) covers the maintenance inspection, repair, alteration, relocation, and reconstruction of such tanks. It is a performance-based inspection with the time between inspections being 10 years or more for out-of-service inspections and 5 years or less for in-service inspections. The scope of this API publication is limited to the tank foundation, bottom, shell, structure, roof, attached appurtenances, and nozzles to the face of the first flange, first threaded joint, or first welding-end connection. While it can be used for inspecting shop-fabricated tanks, it is mainly intended for field-erected ASTs. It is also used for many of the military's large, bulk underground storage tanks. In September 2000, the Steel Tank Institute (STI SP001) published a standard for inspection and repair of shop-fabricated steel tanks. The STI standard addresses double wall tanks and tanks with integral secondary containment pans as well as horizontal tanks; none of these tanks are within the scope of API 653. This standard includes a risk-based approach to inspections, where tanks with the most risk requiring more frequent inspections. The risk-based approach is a function of the size, containment, release prevention and detection, and corrosion history of the tank.

In 1988, the U.S. Environmental Protection Agency (EPA) Code of Federal Regulations (CFR) 40 CFR Part 280 and 40 CFR Part 112 mandated industry standard inspections on tanks and piping that have the potential of impacting the environment as the result of a product release due to a leak or a tank or pipe failure. Each state has implemented this regulation with the EPA standards establishing the minimum requirements. Large, bulk underground and all aboveground storage tanks were excluded from the integrity parts of the regulation. Until recently, only a few states regulated the inspection of these large tanks for integrity. The Spills Prevention Controls and Countermeasures Program (SPCC) generally controls the inspection of petroleum facilities containing ASTs or bulk USTs. Recently, the guidelines for periodic inspection of these large tanks has become mandatory. The petroleum industry has been performing inspections on their tanks for many years, because it is the criterion by which a facility is judged when tank release or tank failure incidents occur.

API Recommended Practice 580 describes the elements of a risk-based approach to an inspection program. It provides the guidance for developing, implementing, and maintaining a risk-based inspection (RBI) program. The guidelines include the means for assessing the program and its plan, while emphasizing safe and reliable operations. The ultimate goal of an internal inspection is the safety and reliability of the operating facilities. A risk-based approach, which takes into account the probability of a failure and the consequence of a failure, can be used to set better intervals between inspections. This approach acknowledges that it is important to focus the highest efforts and resources on addressing maintenance and repairs on those facilities needing it most. By focusing these efforts where they are needed most, more problems will be found earlier and the facilities will be operated safer and less expensively. A risk-based approach also saves money and a permits better use of the operational facilities, because they do not need to be taken out of service before it is necessary. The routine time interval, which has been the practice, can be very costly and may result in less than optimal maintenance and repair. A risk-based approach will better prioritize and manage the tank inspection program. The method and apparatuses of the present invention describe such an approach for determining the time interval between inspections, including an estimate of how long a scheduled inspection can be postponed. The method and apparatuses of the present invention are very measurement oriented, and, as such, will achieve better acceptance by the regulators and the facility operators.

As stated above, there are basic two types of inspections: an in-service and an out-of-service. The in-service inspection requires an inspection of the external parts of the tank, including the tank shell and the chime, while an out-of-service inspection requires both internal and external inspection, including the tank floor. In general, API 653 and most regulatory agencies require an out-of-service inspection every 10 years unless the tank is in good shape, the corrosion rate is low, and the minimum required thickness of the tank floor will not be exceeded in 10 years. An out-of-service inspection is very expensive, not only because of the inspection itself, but the loss of the tank for operations during the inspection, repairs, and maintenance activities. An in-tank inspection, which is normally performed every five years, is less expensive, because the inspection can be performed on those parts of the tank that are visually and easily accessible.

API and others have developed a formula for quantifying the Minimum Remaining Thickness (MRT) of the bottom of the tank after a floor inspection and any necessary repairs have been made:

$$MRT = \{\text{Minimum of } RT_{bc} \text{ or } RT_{ip}\} - O_r(StP_r + UP_r)$$

where
MRT: Minimum remaining thickness at the next inspection
$O_r$: Interval to the next inspection in years
$UP_r$: Underside corrosion rate before repairs
$StP_r$: Internal corrosion rate before repairs
$RT_{bc}$: Minimum remaining thickness from underside corrosion after repairs
$RT_{ip}$: Minimum remaining thickness from internal corrosion after repairs Thus, if we assume that we want the floor to have a minimum thickness of at least 0.1 in. (MRT=0.1 in.), we can compute the interval between inspections, or if we measure or know $UP_r$, $StP_r$, $RT_{bc}$, and $RT_{ip}$. If $UP_r$=0.135 in./year and $StP_r$=0.0034 in./year based on the corrosion rate determined from the previous inspection, and if $RT_{bc}$=0.135 in. and $RT_{ip}$=0.170 in. after repairs have been made, then $O_r$=6.03=6 years. These thickness and corrosion data can obtained from UT floor thickness measurements and magnetic flux floor measurements. The present method and apparatuses make a very good estimate of this thickness during the Extension Time.

The method and apparatuses of the present invention is motivated by the need to better manage out-of-service tank inspection, maintenance, and repair activities in aboveground storage tanks and large, bulk underground bulk tanks, and pertains to all types of products/liquids and all types of tanks (e.g. production, refined petroleum, and chemical tanks). The method and apparatuses are aimed at supporting and help better managing planned annual facility inspection, repair, maintenance, and repair programs. In general, each tank facility plans to perform an inspection on one or more tanks each year so that all tanks undergo an inspection each 10 years. Longer inspection intervals are possible (e.g. 20 years) based on the corrosion rate determined in an API 653 inspection. In many facilities and for most regulatory requirements, the selection of the tanks to undergo an out-of-tank inspection is done on a time basis. Risk-based inspection assessments are used to better focus, prioritize, and manage the efforts on tank inspection programs so that the focus is on those areas of tank integrity with the highest risk. A risk-based approach to tank inspection permits better and more informed decisions about the need, priority, and schedule for inspections. As stated in API 580, a risk-based inspection needs to estimate both the likelihood of a failure and the consequence of the failure. The former is difficult to estimate because of the limited access to the inside of the tank, particularly the floor of the tank, between out-of-service inspections. Corrosion to the bottom and top of the tank floor can lead to failure and leakage. The latter is easier to estimate because one can more easily estimate the maintenance and repair costs, costs due to the loss of operations, and the cost due to cleanup/remediation if a tank fails or leaks. However, the necessary data needed to estimate the likelihood of a failure is difficult to obtain. The main problem is determination of the condition of the tank floor. This information is difficult to obtain because access to the inside of the tank is limited. If it can be determined that the tank floor is in good condition, i.e. adequate thickness, no holes or cracks, and a low-rate of corrosion, then the time between inspections can be increased and more focus can be placed on those tanks in a poorer condition.

If a facilities manager plans to take 4 tanks out of service each year, the important questions to ask are:

(1) Which tanks in the facility should be inspected first, because they are in most need of maintenance and/or repair?
(2) Does each of these tanks selected for an out-of-service inspection need to be done at this time or can the inspection be postponed because the tank is in good shape?
(3) Given that a number of tanks are scheduled for an inspection, which tanks should be inspected first?

The proposed method and apparatuses give the tank owner and operator a method for determining the priority and best schedule for tank maintenance. It is very expensive to take a tank out of service and to perform an inspection. The costs include the cost of the inspection itself and the lost operational benefit of the tank. This is especially true for small tank facilities where one or more products cannot be serviced. Once the out-of-service inspection is complete and the tank it returned to service, the tank must have sufficient floor thickness to avoid structural failure until the next inspection. The minimum thickness of the floor between now and the next inspection needs to be greater than 0.1 in. for tank bottoms and foundations with no means for detection and containment of a bottom leak. The minimum thickness is less (0.05 in.) for tanks with bottom and foundation designs with a means to provide detection and containment of a bottom leak if one were to occur.

Regular in-service inspections are performed on most tanks. These inspections are typically conducted every 5 years and address the condition of the accessible portions of the tank. Visual inspection is a very important part of this process. UT measurements of the thickness of the shell are routinely made to insure the tank has sufficient wall thickness (i.e. strength) to support the product. Unfortunately, most problems occur in the tank floor where visual access is not possible without tanking the tank out of service, removing the product from the tank, and cleaning the tank. As a consequence, the interval between tank inspections is typically set based on a schedule and/or the rate of corrosion estimated from a previous tank inspection. More recently, risk assessment procedures have also been developed to determine this interval. Typically, the time interval between inspections is 10 years although longer intervals may be possible for tanks in good shape. The basic internal inspection procedure (API 653, API12R, or STI SP001) is designed to insure that the structure is in good shape (i.e. not corroding) with the walls, floor, and appurtenances having adequate thickness to structurally support tank operations until the next inspection. As stated above, API 580 has established the guidelines for implementing a tank inspection with the goal of establishing meaningful and cost-effective intervals for inspections. However, they have not specified methods or acceptable approaches. They acknowledge that tanks that have the potential for being in poor shape should be inspected more frequently than tanks in good shape. The difficulty has been to meaningfully assess the condition of the tank and to meaningfully set a safe inspection interval.

There have been a number of approaches for assessing the condition of the tank, for better prioritizing which tanks should be inspected first, and for safely and reliably extending the time between inspections.

The main methods used to justify extending the time between inspections have been AE methods. For example, a number of methods using the AE inspection method called TANKPAC™ by Physical Acoustics have been developed and evaluated. Up to 4 years are possible with these methods. Generally, 12 AE sensors are mounted on the external wall of an AST, and the data is collected and analyzed after a 24-h waiting period for the tank to become acoustically quiet. This method is expensive to use and requires a high degree of technician skill to obtain accurate results. Furthermore, AE methods do not measure floor thickness and are not reliable as leak detection methods. In addition, these methods are not generally accepted in all circles. However, extensive field evaluations where full out-of-service internal inspections have followed such AE measurements, it is clear when certain results are obtained there is a very high probability that the tank is in good shape. If combined with a leak detection method and/or a local measurement of floor thickness, a strong basis for extending the interval between inspections is provided. These methods have been extensively used in many countries of the world. Other types of that assess the rate of corrosion from LRUT sensors placed on the outside wall floor have also been used. The main issue is that AE methods do not measure floor thickness and as a consequence, corrosion rates and floor thickness cannot be accurate evaluated. However, the method of the present invention can utilize the strongest part of the test (i.e. when the AE system indicates no damage), the spatial distribution of the corrosion activity, and the leak detection capability as an element in the method that benefits greatly from actual floor measurements.

Loo [1999] reported on a study of 148 aboveground storage tanks inspected using an AE method (TANKPAC™ produced by Physical Acoustics) of assessing the corrosion activity in the floor of an aboveground storage tank while in-service. The AE results for each of these 148 tanks were compared to the results of an internal tank floor inspection performed as part of an out-of-service inspection. Of the 148 tanks, 33 were crude tanks and 115 were refined product tanks. The results were summarized in FIG. 2 of Loo's paper. The results of the internal inspections (i.e., the actual or true condition of the tank) were reported in terms of four categories (FU1, FU2, FU3, and FU4). The results of the AE tests, which were reported in teens of five corrosion grades from A to E (as defined below), were compared to the out-of-service inspection results. The definitions of the AE Test Results and the Out-of-Service Internal Inspections are given below:

| AE Test Results | Maintenance and Repair |
|---|---|
| A: Very minor | No maintenance necessary |
| B: Minor | No maintenance necessary |
| C: Intermediate | Some maintenance is needed |
| D: Active | Give priority in maintenance schedule |
| E: Highly active | Give highest priority in maintenance schedule |
| Out-of-Service Internal Inspection Results | |
| FU1: No damage/No repair | (A) |
| FU2: Minor damage/No repair | (B, some C) |
| FU3: Damage/Some repair | (D, some C) |
| FU4: Damage/Major repair/New floor | (E) |

As will be described below, there is some uncertainty on how to compare the results of the 5 AE Test Results with the four Internal Inspections, mainly with respect to Grade C and FU2 and FU3.

As described by Loo, the AE method is intended to distinguish good tanks from bad tanks and is a really considered a sorting technique as applied. Table 1 summarizes the results obtained from FIG. 2 of Loo. The table illustrates some very important conclusions about (1) the overall condition of the tanks in the population and (2) the overall reliability of the AE method. Depending on the actual results of the AE test, it can be very reliable in supporting the tank assessment either as applied by Loo or as applied in the present invention. However, in general, our assessment of these results concludes that the AE method leads to correct decisions about the condition of the tank floor only 76.7% of the time with a probability of false alarm of 14.5% and a probability of missed detection of 8.8%. Even the correct decisions are not easy to determine because false alarms and missed detections happens for all grades except A.

When the results of the AE test indicate an A grade, there is a high level confidence that the rate of corrosion of the tank is low and no maintenance or repair of the tank is required. This accounted for 30.5% of the tanks evaluated, i.e., about 1 in 3 tanks tested. Furthermore, when the results of the AE test indicate a B grade, there is also a high level of confidence about the rate of corrosion being low with no maintenance or repair required, but at least 4, and up to 6, of the 41 tests results classified as a B grade are actually missed detections. It is difficult to determine how to interpret the C grade and the FU3 test results, because as defined the FU3 should be equated to a D grade, but the results tend to show many of the FU3 tests are C grades. In general, for our analyses in Table 1, we have assumed about half of the FU3 test results are missed detections and half would be included with the FU1,2 test results as we might expect from the definitions.

Five of the D and E grades were actually assessed as FU1,2 tanks and were judged to be in very good condition, i.e. false alarms. Ten of the tests graded as a B were actually assessed as FU3 and FU4 where damage has occurred, i.e., missed detections. Thus, how the AE test results are used in the method of the present invention is very dependent on the actual results of the AE test. More reliability can be assigned to the AE test results when a local UT floor thickness measurement is used to help interpret the results. Also, more reliability can be assumed if a more advanced signal processing method is used to determine the grade.

As stated above, strong statements can be made when an A or B grade is determined, particularly for an A grade. This is not the case for D and E grades, because there are almost as many tanks in need of repair and maintenance as prescribed by FU4 that receive a B or C grade vice a D or E grade. If the AE test results indicates a problem, you would be correct only 38.1% of the time. Similarly, if the AE results were A, B, or C, you would miss 9 of the 123 tanks (7.3%) in need of serious maintenance and repair and possibility more if the tanks with a C grade need some repair. Thus, we would consider the results of a previous API 653 inspection to be more reliable than a current AE inspection if the results of the AE test were D or E.

Some general conclusions about the condition tanks in general can be made from Table 1, which can support the overall method. First, 64.2% of the tanks tested need little or no maintenance or repair. Thus, there is almost a 2 in 3 chance that any tank that passes a Leak Test is in good shape. Second, 14.2% of the tanks tested need significant maintenance and repair. Thus, a Leak Detection Test will correctly identify 78.4% of the tank conditions. This leaves 21.6% as uncertain with more information needed to ascertain their true condition. In general, we would expect that almost all of these 21.6% of the tanks would pass a Leak Detection Test even though they still need some repair and/or some maintenance. Thus, some measurement of the tank floor condition is needed in addition to the AE test.

TABLE 1

Summary of the AE Corrosion Activity Tests [Source: Loo, (1999)].

| AE Grade | % of Tanks | Number of Tanks | Cum % of Tanks | FU1/2 | FU3 | FU4 | | FU1/2 | FU3 | FU4 | |
|---|---|---|---|---|---|---|---|---|---|---|---|
| A | 30.5% | 45 | 30.5% | 100.0% | 0.0% | 0.0% | 100.0% | 45 | 0 | 0 | 45 |
| B | 27.5% | 41 | 58.0% | 76.0% | 14.0% | 10.0% | 100.0% | 31 | 6 | 4 | 41 |
| C | 25.0% | 37 | 83.0% | 38.5% | 48.5% | 13.0% | 100.0% | 14 | 18 | 5 | 37 |
| D | 7.5% | 11 | 90.5% | 18.5% | 45.0% | 36.5% | 100.0% | 2 | 5 | 4 | 11 |
| E | 9.5% | 14 | 100.0% | 21.0% | 21.0% | 58.0% | 100.0% | 3 | 3 | 8 | 14 |
| | 100.0% | 148 | | | | | 500.0% | 95 | 32 | 21 | 148 |
| | | | | | | | | 64.2% | 21.6% | 14.2% | 100.0% |

TABLE 1-continued

Summary of the AE Corrosion Activity Tests [Source: Loo, (1999)].

| AE Grade | Correct Decision | | Incorrect Decision | | False Alarms | | Missed Detections | |
|---|---|---|---|---|---|---|---|---|
| A | 45 | 100.0% | 0 | 0.0% | 0 | 0.0% | 0 | 0.0% |
| B | 31 | 75.6% | 10 | 24.4% | 10 | 24.4% | 0 | 0.0% |
| C | 23 | 62.2% | 14 | 37.8% | 9 | 24.3% | 5 | 13.5% |
| D | 6.5 | 59.1% | 5 | 40.9% | 3 | 22.7% | 2 | 18.2% |
| E | 8 | 57.1% | 6 | 42.9% | 0 | 0.0% | 6 | 42.9% |
|   | 114 | 76.7% | 35 | 23.3% | 22 | 62.3% | 13 | 37.7% |
|   | 76.7% |   | 23.3% |   |   |   |   |   |

Cole and Gautrey [2002] described history of the AE method used in the Loo study (TANKPAC™ produced by Physical Acoustics) and included additional data and illustrations of the use of the method for ascertaining the condition of a tank and whether or not the time between scheduled internal inspections can be extended. Their FIG. 10 increased the number of tanks used in Table 1 from 148 to 157; the results were very similar. In their FIG. 11, they reported the results of a similar study by the French Institute of Petroleum for a sample population of 78 tanks with very similar results. Table 2 compares the results from Loo, Cole and Gautrey, and the French Institute of Petroleum and shows that they are very similar. The main conclusions hold: (1) tanks with AE reported grades of A and B (FU1,2) show very little or some maintenance and repair required, (2) tanks with AE reported grade of D and E showed large damage (FU4) with a high degree of maintenance and repair needed, (3) a small number of false alarms in which AE reported grades of D and E were actually in good shape (FU1,2) or not in very bad shape (FU3), and (4) no missed detections in which tanks in very bad shape (FU4) were reported in good shape. The strongest statements that can be made about the AE test is that if a test results in a grade of A or B, it should be in good shape. Conversely, if a tank is reported with a grade of D or E, it should be treated as such even though about half of the tanks in this category were actually in moderate to good shape.

TABLE 2

Summary of the AE Corrosion Activity Test Results from Three Sources.

| AE Grade | Loo (1999): 148 Tanks | | | French Institute of Petroleum (2002): 78 Tanks | | | Cole and Gautrey (2002): 157 Tanks | | |
|---|---|---|---|---|---|---|---|---|---|
|   | FU1/2 | FU3 | FU4 | FU1/2 | FU3 | FU4 | FU1/2 | FU3 | FU4 |
| A | 100.0% | 0.0% | 0.0% | 100.0% | 0.0% | 0.0% | 100.0% | 0.0% | 0.0% |
| B | 76.0% | 14.0% | 10.0% | 89.0% | 11.0% | 0.0% | 80.5% | 11.5% | 8.0% |
| C | 38.5% | 48.5% | 13.0% | 22.0% | 18.0% | 60.0% | 36.0% | 40.0% | 24.0% |
| D | 18.5% | 45.0% | 36.5% | 19.0% | 29.5% | 51.5% | 15.0% | 45.0% | 40.0% |
| E | 21.0% | 21.0% | 58.0% | 3.0% | 14.0% | 92.0% | 12.0% | 26.0% | 62.0% |

Mejia, Hay, Mustafa, and Santa Fe [2009] described a method of using AE to extend the time between scheduled inspections. Their Tables 2 and 3 summarize the application of their method, which combines the Overall Corrosion Grade A through E with a Potential Leak Detection Grade. The Potential Leak Detection Grade indicates areas of highly concentrated clusters of AE events, where 5 indicates very high potential and 1 indicates very low potential. Unlike the present method of this invention, this method does not specifically test for a leak. Table 3 summarizes their results. The schedule for an internal inspection can be postpone up to 4 years for A, B and 1, 2 grades, up to 2 years for C, D, E and 1 and most 2 grades, as well as A, B and 1, 3, 4 grades. A postponement of 0.5 and 1 year is possible for all but D, E and 5 grades. The method of the present invention allows extensions up to 5 years and has more reliability in the decision process, because the present method is based on whether or not a tank is leaking as determined from a Leak Detection Test and what the thickness and corrosion rate of the floor is from actual measurements. The data from the AE test as included in the method of the present invention can also be used to test the tank floor for leaks.

TABLE 3

Summary of the AE Corrosion Activity Test Interpretation in terms of the number of years extension for a potential leak grade and a Corrosion grade [Source: Mejia, Hay, Mustafa, and Santa Fe (2009)].

| Potential Leak Grade | Overall Corrosion Grade | | | | |
|---|---|---|---|---|---|
|   | A | B | C | D | E |
| 1 | I | I | II | N/A | N/A |
| 2 | I | I | II | N/A | N/A |
| 3 | II | II | III | III | N/A |
| 4 | II | III | III | IV | IV |
| 5 | III | III | IV | IV | IV |

TABLE 3-continued

Summary of the AE Corrosion Activity Test Interpretation in terms of the number of years extension for a potential leak grade and a Corrosion grade [Source: Mejia, Hay, Mustafa, and Santa Fe (2009)].

| Potential Leak Grade | Overall Corrosion Grade | | | | |
|---|---|---|---|---|---|
|   | A | B | C | D | E |
| 1 | 4 | 4 | 2 | N/A | N/A |
| 2 | 4 | 4 | 2 | N/A | N/A |
| 3 | 2 | 2 | Schedule | Schedule | N/A |

TABLE 3-continued

Summary of the AE Corrosion Activity Test Interpretation in terms of the number of years extension for a potential leak grade and a Corrosion grade [Source: Mejia, Hay, Mustafa, and Santa Fe (2009)].

| 4 | 2 | Schedule | Schedule | Schedule | Schedule |
| 5 | Schedule | Schedule | Schedule | Schedule | Schedule |

I: Extension Time Interval = 4 years
II: Extension Time Interval = 2 years
III: Extension Time Interval = 1 years
IV: Extension Time Interval = 0.5 years
* or 6 months or 1 Year

SUMMARY OF THE INVENTION

It is the object of this invention to provide a method and apparatuses for safely extending the time between out-of-service inspections using a risk-based approach and the results of a leak detection test and actual measurements of the thickness and corrosion rate of the tank floor.

It is the object of this invention to provide a method and apparatuses for safely extending the time between out-of-service inspections using a Bayesian statistical approach and the results of a leak detection test and actual measurements of the thickness and corrosion rate of the tank floor.

It is the object of this invention to provide a method and apparatuses for safely extending the time between out-of-service inspections using leak detection.

It is the object of this invention to provide a method and apparatuses for safely extending the time between out-of-service inspections using leak detection and previous out-of-service inspections.

It is the object of this invention to provide a method and apparatuses for safely extending the time between out-of-service inspections using leak detection and floor thickness and corrosion measurements made over a small area of the tank.

It is the object of this invention to provide a method and apparatuses for safely extending the time between out-of-service inspections using leak detection, floor thickness and corrosion measurements made over a small area of the tank, and the spatial distribution of floor inspection results from previous out-of-service floor inspection.

It is the object of this invention to provide a method and apparatuses for safely extending the time between out-of-service inspections using leak detection, floor thickness and corrosion measurements made over a small area of the tank, and AE measurements of the corrosion activity in the tank floor.

It is the object of this invention to provide a method and apparatuses for safely extending the time between out-of-service inspections using leak detection, floor thickness and corrosion measurements made over a small area of the tank, and AE measurements of the corrosion activity in the tank floor, and the spatial distribution of floor inspection results from previous out-of-service floor inspections.

The method and apparatuses of the present invention can be used to provide critical data and information between out-of-service inspections for assessing the structural integrity of a tank to determine if a tank is likely to fail or leak. These data and information can be used to better prioritize and better schedule out-of-service tank inspections for aboveground storage tanks as specified by API 653, API12R1, STI SP001, and/or other out-of-service inspections, because it can be used to assess the condition of the tank floor, i.e., the thickness of the tank floor, the rate of corrosion of the floor, and whether or not any holes or cracks exist in the floor. If the floor is in good condition, then it is possible to postpone a scheduled inspection or to extend the time between inspections so that the maintenance and repair activities can focus on those tanks with the most need.

It is comprised of a leak detection test and one or more actual measurements of the thickness and corrosion condition of the bottom floor of the tank in a least one section of the tank. This approach will work well for tanks in which the corrosion is either small or relatively uniform. If not, information about the spatial distribution of floor thickness and corrosion rate is needed to better use these data. This spatial information can be obtained (1) the most recent API 653, AP12R1, or STI SP001 thickness measurements of the floor of the tank using UT and/or magnetic flux or eddy current measurements, and/or (2) an AE inspection of the tank floor to assess the corrosion condition of the tank floor.

The preferred method of measuring thickness of the tank floor is to use one or more ultrasonic (UT) thickness probes on a vertical staff that is inserted into the tank from an opening at the top of the tank. The AE inspection can be performed by placing three or more sensors on the wall of the tank or in the product inside the tank on the staff used to make the UT floor thickness measurements, where at least one of the sensors is at a different elevation than the other sensors. All of these proposed measurement procedures have been used for tank integrity assessments for many years, but they have not been used in combination or for in-service inspections. The proposed method and apparatuses make it possible to prioritize the order for tank inspections and to postpone out-of-service inspections safely for a period of time without taking the tank out of service, by using well understood methods of integrity inspection, and with a high probability that the tank will not structurally fail or leak during the extension period.

The preferred method and apparatus of the present invention is comprised of a mass-based leak detection test (LRPD) with the sensor tube inserted into the tank an at convenient opening from the top of the tank, a set of at least three ultrasonic thickness sensors on an arm attached to the leak detection sensor tube, and either the results of a previous out-of-service inspection of the tank floor via API 653, API12R1, STI SP001 or other approved method and/or a set of three AE sensors located near the bottom of the tank with one of the sensors located at a different elevation from an arm attached to the tube and in a different plane than the other two sensors. The Extension Time Interval will depend on the number of tests conducted and the results of these tests and previous measurements. A passing leak detection result with a reliable leak detection method provides the basis for postponing or extending the time interval an out-of-service inspection. Without any other tests or information about the condition of the tank, the time interval between inspections can be extended a year, which is the time required between tightness test specified by the EPA for smaller tanks to insure their integrity. With floor thickness measurements and some assessment of the spatial distribution of the thickness and corrosion of the tank floor, longer time intervals (e.g. 2 to 5 years) are possible depending on the extent of the testing and the results of the testing.

IN THE DRAWINGS

DETAILED DESCRIPTION OF THE INVENTION

Figure 1:
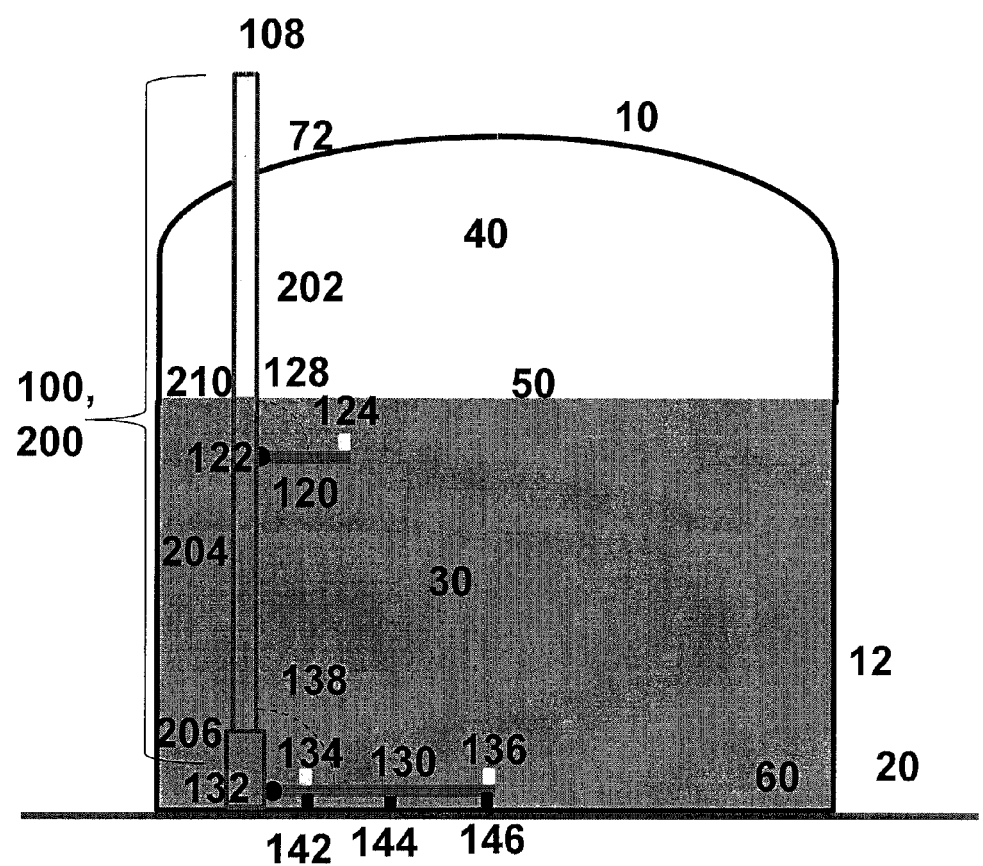
FIG. 1 illustrates the preferred method and apparatus of the present invention with an in-tank floor thickness and an in-tank corrosion assessment system integrated with the mass-based leak detection system.

The method and apparatuses of the present invention can be used to provide critical data and information about the structural integrity of an aboveground or bulk underground storage tank needed to better prioritize and better schedule out-of-service tank inspections for these tanks, because it can be used to assess the condition of the tank floor, i.e., the thickness of the tank floor, the rate of corrosion of the floor, and whether or not any holes or cracks exist in the floor. If the floor is in good condition, then it is possible to postpone a scheduled inspection or to extend the time between inspections so that the maintenance and repair activities can focus on those tanks with the most need.

The method is comprised of a leak detection test and one or more actual measurements of the thickness and corrosion condition of the bottom floor of the tank in a least one section of the tank. This approach will work well for tanks in which the corrosion is either small or relatively uniform. If not, information about the spatial distribution of floor thickness and corrosion rate is needed to better use these data. This spatial information can be obtained from (1) thickness measurements of the floor of the tank using UT and/or magnetic flux or eddy current measurements made in previous out-of-service inspections according to API 653, AP12R1, or STI SP001, and/or (2) an AE inspection of the tank floor to assess the corrosion condition of the tank floor. The method and the apparatuses of the present invention provide important data to risk-based inspection assessments.

If an API 653 floor inspection was conducted previously, the results of this inspection can be used to increase the confidence in the risk assessment performed to determine if a scheduled tank inspection can be extended without risk of tank failure or a leak. The bottom inspection gives the results of bottom thickness measurements on all plates comprising the floor. Each plate can have a different rate of corrosion or initial thickness. The rate of corrosion can vary because of some inhomogeneity in the soil beneath the tank that accelerates local corrosion on the external or underneath side of the bottom or some local pools of water on the inside of the tank due to deflection in the tank floor. A complete floor inspection according to API 653 will identify such local pockets of accelerated corrosion. This information can be used to make a more conservative estimate of the corrosion rate for future local measurements of bottom thickness on one or a limited number of plates. This is really conservative since once these problem areas are identified, they are usually addressed as part of the API 653 inspection before the tank is brought back into service for another 10-year period. Even so, the UT thickness data provided during the tank test is used to estimate the corrosion rate between the last thickness measurement in the same location can be used to re-estimate the rate of corrosion at all of the previous measurements by the ratio of the local UT measurement and the previous API floor inspection measurements. Thus, if in the previous API 653 Inspection a corrosion rate of 0.035 in./year was estimated and the UT thickness measurement is different (higher or lower), the ratio of the corrosion rate measured with the UT sensor and the previous corrosion rate can be used to forecast the corrosion rate in the tank using the largest rate measurement in the previous API inspection. This corrosion rate can be used to extend the interval between inspections until the minimum plate thickness is met. This computation is really conservative, because it assumes that none of the corrective action taken at the last API 653 Inspection was of any value.

Figure 2:
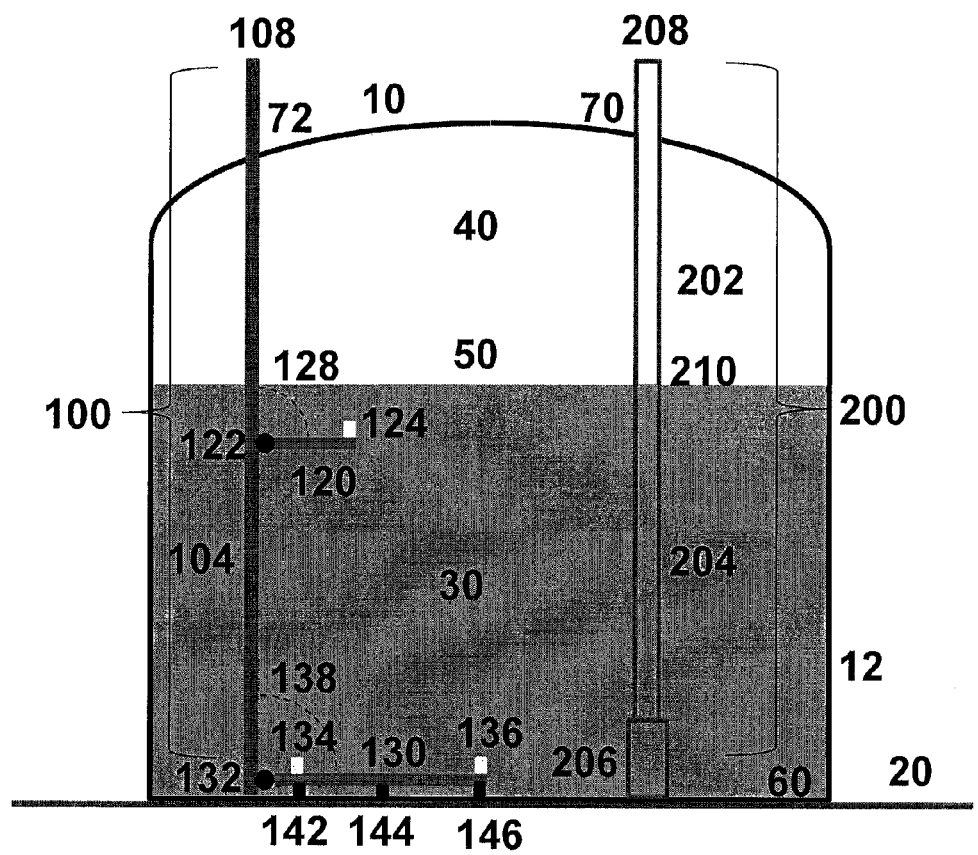
FIG. 2 illustrates the preferred method and apparatus of the present invention with an in-tank floor thickness and an in-tank corrosion assessment system separated from the mass-based leak detection system.
Figure 3:
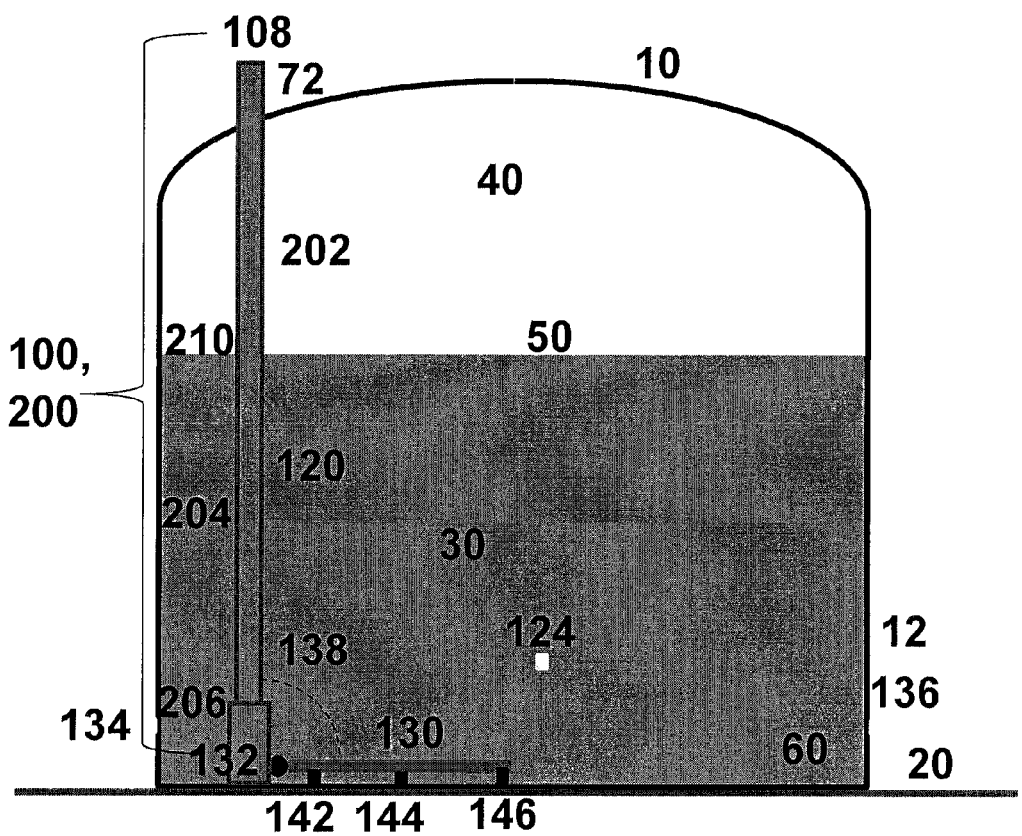
FIG. 3 illustrates an alternative embodiment of the preferred method and apparatus of the present invention with an in-tank floor thickness system integrated with the mass-based leak detection system and combined with an external walled-mounted corrosion assessment system.
Figure 4:
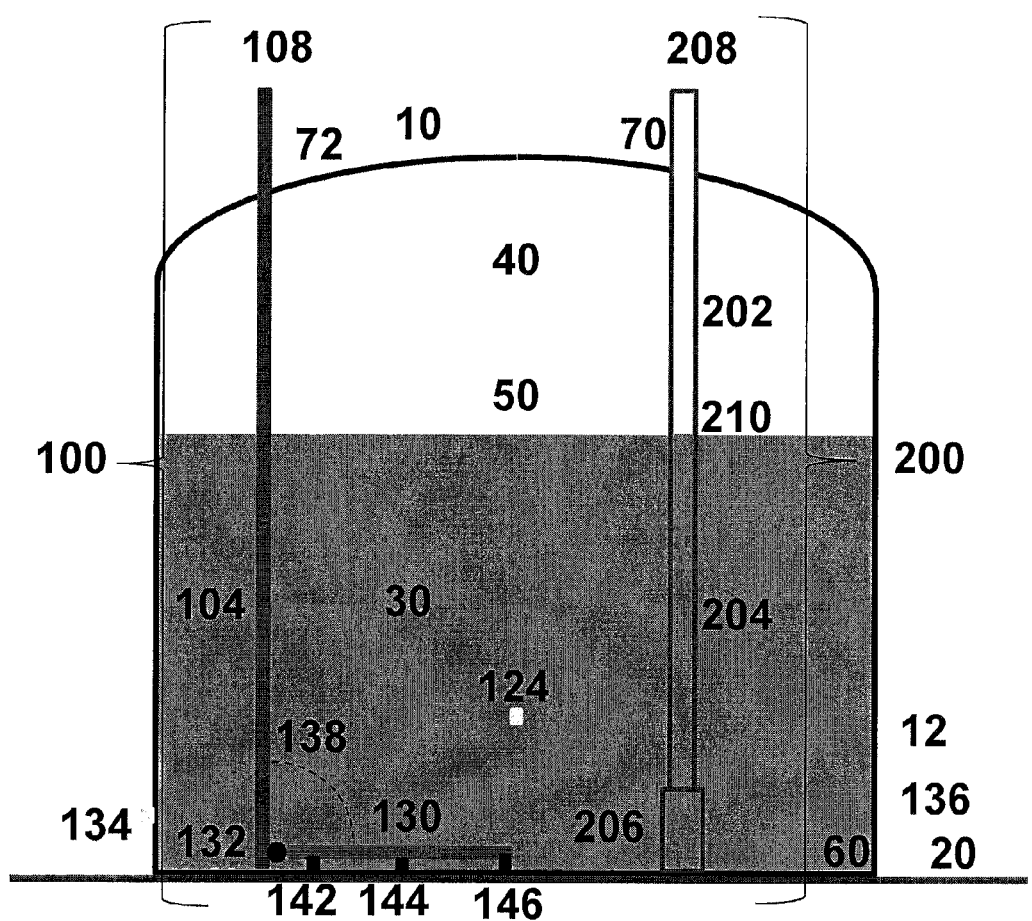
FIG. 4 illustrates an alternative embodiment of the preferred method and apparatus of the present invention with an in-tank floor thickness system separated from the mass-based leak detection system and combined with an external walled-mounted corrosion assessment system.

FIG. 1 illustrates the preferred method and apparatus of the present invention. It is comprised of a mass-based leak detection test (LRPD) 100 inserted into the tank 10 an at convenient opening 72 at the top of the tank, a set of at least three ultrasonic thickness sensors 142, 144, 146 on an arm 130 attached to the leak detection sensor tube 204, 206, and either the results of a previous out-of-service inspection of the tank floor via API 653, API12R1, STI SP001 or other approved inspection method and/or a set of three AE sensors 124, 134, 136 located near the bottom 60 of the tank 10 with one of the sensors 124 located at a different elevation from an arm 120 attached to the tube 204 and in a different plane than the other two sensors. FIG. 2 illustrates a very similar but alternative embodiment where the leak detection system 200 is separated from the UT and AE measurement system 100 and is inserted into a different opening 70 at the top of the tank. Both embodiments will produce very similar results. FIGS. 3 and 4 illustrate measurement configurations similar to FIGS. 1 and 2 except the AE sensors 124, 134, 136 are mounted on the outside wall 12 of the tank 10, where one of the sensors 124 is mounted at a different elevation than the other sensors. The elevation difference for AE measurements from both the internal and external sensor location allows for acoustic signals generated on the surface 50/top 40 part of the tank to be distinguished from acoustic signals generated from the floor 60 of the tank. This prevents false alarms on the surface due to condensation drips.

The preferred method of measuring thickness of the tank floor is to use one or more ultrasonic (UT) thickness probes that make contact with the floor and AE sensors that detect the presence of corrosion noise (or leaks) that propagate through the liquid product. The AE sensors can be placed on the external wall of the tank, or inserted in the product inside the tank on the staff used to make the UT floor thickness measurements, where at least one of the sensors is at a different elevation than the other sensors and not in the same vertical plane. The preferred configuration is three sensors mounted in the liquid inside the tank as illustrated in FIG. 1 or 2. Additional floor thickness measurements can be made by adding one or more additional UT sensor systems anus 130 at the bottom of the leak detection system in FIGS. 1 and 3 or to the bottom 130 of the staff 104 in FIGS. 2 and 4. Additional UT measurements can be most easily made with any of the two basic configurations by rotating the leak detection tube 204 or the mounting staff 104. This is possible because the UT measurements can be made in less than 1 min.

Figure 5:
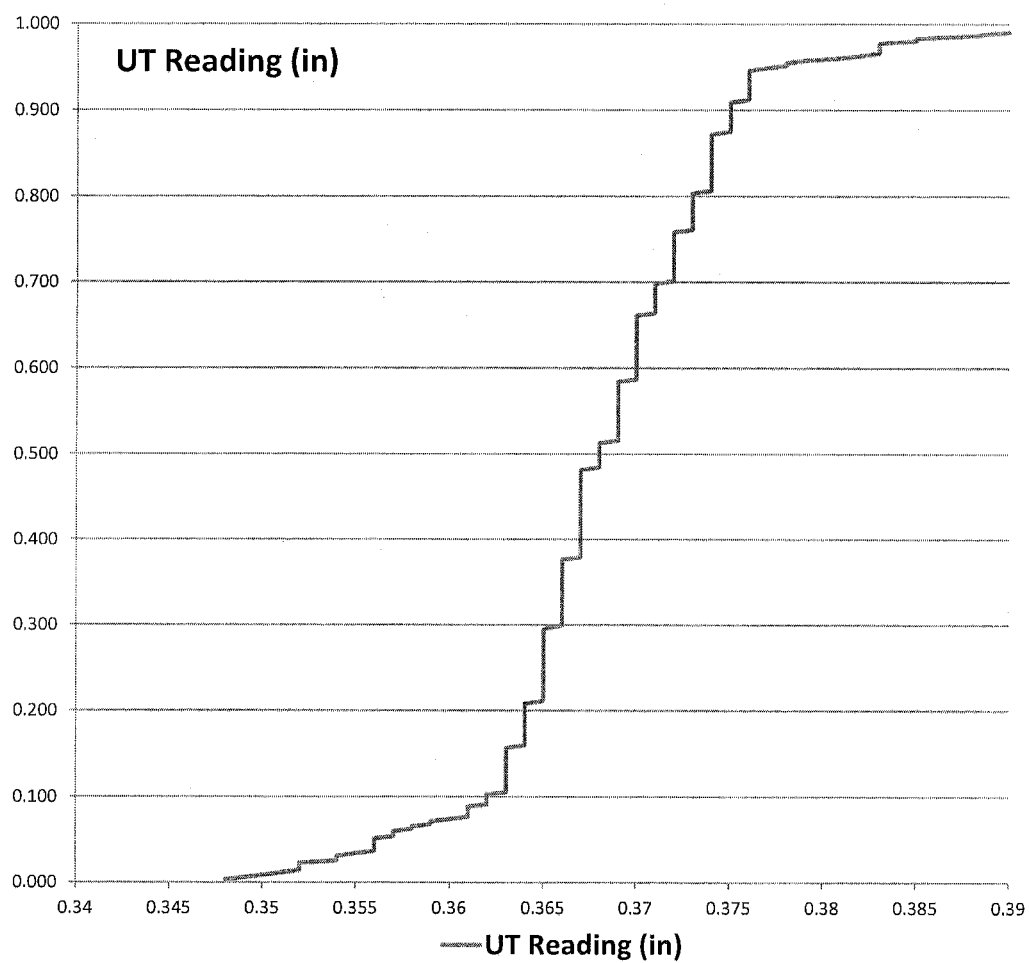
FIG. 5 illustrates a cumulative frequency distribution (CFD) of floor thickness in an aboveground tank. The distribution is normally distributed and three standard deviations would normally predict the lowest and highest floor thickness.
Figure 6:
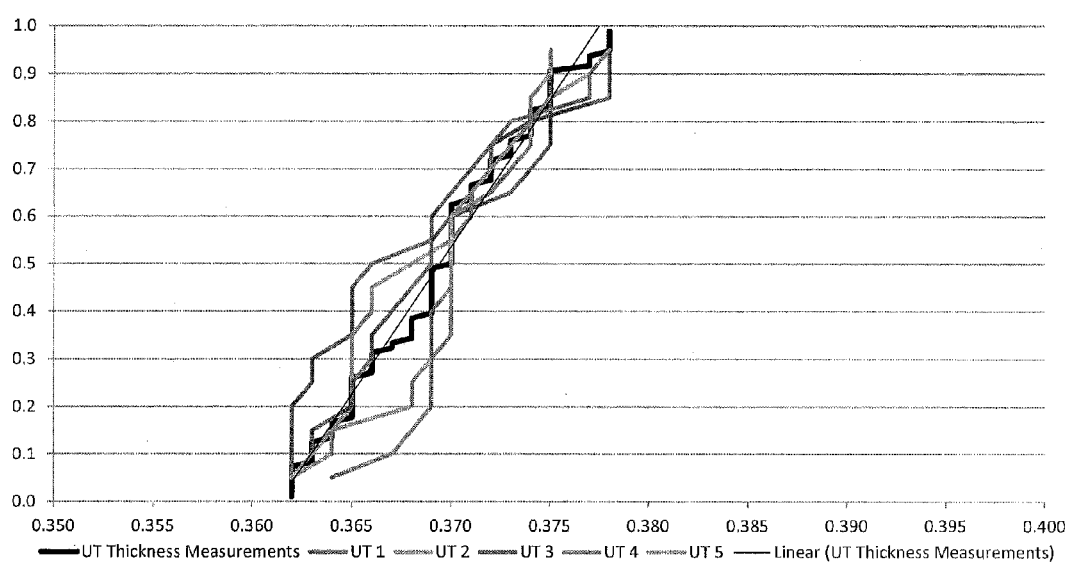
FIG. 6 illustrates the CFDs of the floor thickness of the five aboveground storage tanks analyzed.

An analysis of the out-of-service, internal inspection of the floor of the tank obtained using the UT sensor thickness data was performed to determine if a small sample (i.e., 3 to 6) could be used to accurately estimate the minimum thickness and the maximum corrosion rate of the tank floor using a small number of UT measurements obtained in a local area of the tank when there were no local hot spots or high areas of corrosion. Approximately 4 or more UT thickness measurements were made per tank floor panel. We analyzed the inspections from five large USTs with ages ranging from 13 to 15 years old and diameters of 69.7 ft (3 tanks), 37.7 ft (1 tank) and 26.3 (1 tank). Table 4 presents an illustration for one of five cylindrical USTs; the histograms of the data in Table 4 are illustrated in FIG. 5 as a cumulative frequency distribution (CFD). The CFDs of all five tanks in illustrated in FIG. 6. Table 5 presents the results from a 82.5-ft-diameter aboveground storage tank containing 1,040,000 gal that was built in 1976 and last inspected in 2009 (34 years old). The tables summarize the statistics for each panel and for the floor as a whole. The general conclusion is that 3 to 6 UT measurements made on any floor panel or group of floor panels would be sufficient to make a good estimate of the minimum measured thickness and therefore the maximum corrosion rate. This estimate is made from by subtracting 3 times the standard deviation from the mean or median or by just using the minimum UT measurement. This is justified from the Gaussian behavior of the histograms.

The ultimate objective of these measurements is to determine if a scheduled out-of-service inspection should be performed now or can it be postponed so another inspection can be performed. The Extension/Postponement Time Interval will depend on the number of tests conducted and the results of these tests and previous measurements. A passing leak detection result with provides the basis for postponing or extending the time interval of an out-of-service inspection. Without any other tests or information about the condition of the tank, the time interval between inspections can be extended a year, which is the time required between tightness test specified by the EPA for smaller tanks to insure their integrity. With floor thickness measurements and some assessment of the spatial distribution of the thickness and corrosion of the tank floor, longer time intervals are possible depending on the extent of the testing and the results of the testing.

While all of these proposed measurement procedures have been used for tank integrity assessments for many years, they have not been used in combination or for in-service inspections. The proposed method and apparatuses make it possible to prioritize the order for tank inspections and to postpone out-of-service inspections safely for a period of time without taking the tank out of service, by using well understood methods of integrity inspection, and with a high probability that the tank will not structurally fail or leak during the extension period.

TABLE 4

Summary of the statistics of a UT internal inspection of the tank floor for an 65.6-ft diameter, 733,000-gal UST that is 15 years old.

| UT Reading Number | Plate Number | UT Reading (in) | Mean | StdDev | Median | Max | Min | Number |
|---|---|---|---|---|---|---|---|---|
| 1 | 1 | 0.364 | ″0.361 | ″0.006 | ″0.364 | ″0.366 | ″0.352 | ″4 |
| 2 | 1 | 0.366 | | | | | | |
| 3 | 1 | 0.352 | | | | | | |
| 4 | 1 | 0.363 | | | | | | |
| 5 | 1 | 0.363 | ″0.362 | ″0.005 | ″0.363 | ″0.366 | ″0.351 | ″9 |
| 6 | 1 | 0.366 | | | | | | |
| 7 | 1 | 0.359 | | | | | | |
| 8 | 1 | 0.366 | | | | | | |
| 9 | 1 | 0.361 | | | | | | |
| 10 | 2 | 0.358 | | | | | | |
| 11 | 2 | 0.365 | | | | | | |
| 12 | 2 | 0.366 | | | | | | |
| 13 | 2 | 0.351 | | | | | | |
| 14 | 2 | 0.37 | ″0.366 | ″0.011 | ″0.369 | ″0.383 | ″0.354 | ″6 |
| 15 | 2 | 0.354 | | | | | | |
| 16 | 2 | 0.383 | | | | | | |
| 17 | 2 | 0.354 | | | | | | |
| 18 | 2 | 0.367 | | | | | | |
| 19 | 2 | 0.37 | | | | | | |
| 20 | 3 | 0.361 | ″0.369 | ″0.012 | ″0.367 | ″0.388 | ″0.349 | ″8 |
| 21 | 3 | 0.383 | | | | | | |
| 22 | 3 | 0.369 | | | | | | |
| 23 | 3 | 0.365 | | | | | | |
| 24 | 3 | 0.365 | | | | | | |
| 25 | 3 | 0.388 | | | | | | |
| 26 | 3 | 0.349 | | | | | | |
| 27 | 3 | 0.368 | | | | | | |
| 28 | 3 | 0.36 | ″0.366 | ″0.006 | ″0.366 | ″0.374 | ″0.360 | ″4 |
| 29 | 4 | 0.374 | | | | | | |
| 30 | 4 | 0.365 | | | | | | |
| 31 | 4 | 0.366 | | | | | | |
| 32 | 4 | 0.364 | 0.361 | 0.006 | 0.364 | 0.367 | 0.350 | 12 |
| 33 | 4 | 0.365 | | | | | | |
| 34 | 4 | 0.363 | | | | | | |
| 35 | 4 | 0.354 | | | | | | |
| 36 | 4 | 0.367 | | | | | | |
| 37 | 5 | 0.363 | | | | | | |

TABLE 4-continued

Summary of the statistics of a UT internal inspection of the
tank floor for an 65.6-ft diameter, 733,000-gal UST that is 15 years old.

| UT Reading Number | Plate Number | UT Reading (in) | Mean | StdDev | Median | Max | Min | Number |
|---|---|---|---|---|---|---|---|---|
| 38 | 5 | 0.366 | | | | | | |
| 39 | 5 | 0.361 | | | | | | |
| 40 | 5 | 0.35 | | | | | | |
| 41 | 5 | 0.364 | | | | | | |
| 42 | 5 | 0.366 | | | | | | |
| 43 | 5 | 0.352 | | | | | | |
| 44 | 5 | 0.365 | 0.363 | 0.006 | 0.365 | 0.369 | 0.348 | 13 |
| 45 | 6 | 0.367 | | | | | | |
| 46 | 6 | 0.348 | | | | | | |
| 47 | 6 | 0.365 | | | | | | |
| 48 | 6 | 0.356 | | | | | | |
| 49 | 6 | 0.369 | | | | | | |
| 50 | 6 | 0.365 | | | | | | |
| 51 | 6 | 0.362 | | | | | | |
| 52 | 6 | 0.357 | | | | | | |
| 53 | 6 | 0.367 | | | | | | |
| 54 | 6 | 0.365 | | | | | | |
| 55 | 7 | 0.364 | | | | | | |
| 56 | 7 | 0.365 | 0.364 | 0.003 | 0.365 | 0.367 | 0.356 | 13 |
| 57 | 7 | 0.364 | | | | | | |
| 58 | 7 | 0.366 | | | | | | |
| 59 | 7 | 0.363 | | | | | | |
| 60 | 7 | 0.367 | | | | | | |
| 61 | 7 | 0.356 | | | | | | |
| 62 | 7 | 0.363 | | | | | | |
| 63 | 8 | 0.365 | | | | | | |
| 64 | 8 | 0.363 | | | | | | |
| 65 | 8 | 0.3652 | | | | | | |
| 66 | 8 | 0.366 | | | | | | |
| 67 | 8 | 0.364 | | | | | | |
| 68 | 8 | 0.367 | | | | | | |
| 69 | 8 | 0.366 | 0.364 | 0.005 | 0.365 | 0.373 | 0.352 | 13 |
| 70 | 8 | 0.365 | | | | | | |
| 71 | 8 | 0.363 | | | | | | |
| 72 | 8 | 0.373 | | | | | | |
| 73 | 9 | 0.365 | | | | | | |
| 74 | 9 | 0.367 | | | | | | |
| 75 | 9 | 0.352 | | | | | | |
| 76 | 9 | 0.365 | | | | | | |
| 77 | 9 | 0.363 | | | | | | |
| 78 | 9 | 0.364 | | | | | | |
| 79 | 9 | 0.365 | | | | | | |
| 80 | 9 | 0.364 | | | | | | |
| 81 | 9 | 0.365 | | | | | | |
| 82 | 9 | 0.364 | 0.364 | 0.005 | 0.366 | 0.369 | 0.357 | 4 |
| 83 | 9 | 0.369 | | | | | | |
| 84 | 9 | 0.357 | | | | | | |
| 85 | 10 | 0.367 | | | | | | |
| 86 | 10 | 0.366 | 0.366 | 0.006 | 0.368 | 0.371 | 0.352 | 8 |
| 87 | 10 | 0.37 | | | | | | |
| 88 | 10 | 0.367 | | | | | | |
| 89 | 10 | 0.352 | | | | | | |
| 90 | 10 | 0.368 | | | | | | |
| 91 | 10 | 0.371 | | | | | | |
| 92 | 11 | 0.368 | | | | | | |
| 93 | 11 | 0.363 | | | | | | |
| 94 | 11 | 0.366 | 0.364 | 0.005 | 0.366 | 0.367 | 0.355 | 6 |
| 95 | 11 | 0.367 | | | | | | |
| 96 | 11 | 0.355 | | | | | | |
| 97 | 11 | 0.367 | | | | | | |
| 98 | 11 | 0.365 | | | | | | |
| 99 | 11 | 0.363 | | | | | | |
| 100 | 12 | 0.365 | 0.362 | 0.004 | 0.364 | 0.366 | 0.356 | 8 |
| 101 | 12 | 0.366 | | | | | | |
| 102 | 12 | 0.356 | | | | | | |
| 103 | 12 | 0.363 | | | | | | |
| 104 | 12 | 0.359 | | | | | | |
| 105 | 12 | 0.366 | | | | | | |
| 106 | 12 | 0.356 | | | | | | |
| 107 | 12 | 0.366 | | | | | | |

TABLE 4-continued

Summary of the statistics of a UT internal inspection of the tank floor for an 65.6-ft diameter, 733,000-gal UST that is 15 years old.

| UT Reading Number | Plate Number | UT Reading (in) | Mean | StdDev | Median | Max | Min | Number |
|---|---|---|---|---|---|---|---|---|
| 108 | 12 | 0.364 | 0.371 | 0.005 | 0.372 | 0.375 | 0.364 | 4 |
| 109 | 13 | 0.371 | | | | | | |
| 110 | 13 | 0.375 | | | | | | |
| 111 | 13 | 0.373 | | | | | | |
| 112 | 14 | 0.366 | 0.370 | 0.005 | 0.368 | 0.378 | 0.366 | 4 |
| 113 | 14 | 0.367 | | | | | | |
| 114 | 14 | 0.378 | | | | | | |
| 115 | 14 | 0.369 | | | | | | |
| 116 | 14 | 0.369 | 0.367 | 0.002 | 0.368 | 0.369 | 0.364 | 4 |
| 117 | 14 | 0.369 | | | | | | |
| 118 | 14 | 0.367 | | | | | | |
| 119 | 14 | 0.364 | | | | | | |
| 120 | 15 | 0.364 | | | | | | |
| | | | Mean | StdDev | Median | Max | Min | Number |
| | | Mean | 0.365 | 0.006 | 0.366 | 0.372 | 0.355 | 0.364 |
| | | StdDev | 0.003 | 0.003 | 0.002 | 0.007 | 0.006 | 0.006 |
| | | Median | 0.364 | 0.005 | 0.366 | 0.369 | 0.355 | 0.365 |
| | | Max | 0.371 | 0.012 | 0.372 | 0.388 | 0.366 | 0.388 |
| | | Min | 0.361 | 0.002 | 0.363 | 0.366 | 0.348 | 0.348 |
| | | Number | 16 | 16 | 16 | 16 | 16 | 120 |
| | | 3 StDev | 0.009 | 0.008 | 0.007 | 0.020 | 0.017 | 0.019 |
| | Mean- | 3 StDev | 0.356 | -0.002 | 0.359 | 0.352 | 0.339 | 0.345 |

TABLE 5

Summary of the statistics of a UT internal inspection of the tank floor for an 82.5-ft diameter, 1,040,000-gal AST that is over 34 years old.

| | READING 1 | READING 2 | READING 3 | READING 4 | READING 5 | Mean | StDev |
|---|---|---|---|---|---|---|---|
| 1 | 0.362 | 0.365 | 0.367 | 0.373 | 0.37 | 0.367 | 0.0043 |
| 2 | 0.375 | 0.378 | 0.371 | 0.369 | 0.368 | 0.372 | 0.0042 |
| 3 | 0.366 | 0.364 | 0.363 | 0.369 | 0.37 | 0.366 | 0.0030 |
| 4 | 0.375 | 0.372 | 0.363 | 0.371 | 0.375 | 0.371 | 0.0049 |
| 5 | 0.363 | 0.365 | 0.365 | 0.367 | 0.368 | 0.366 | 0.0019 |
| 6 | 0.375 | 0.374 | 0.378 | 0.369 | 0.373 | 0.374 | 0.0033 |
| 7 | 0.374 | 0.373 | 0.372 | 0.377 | 0.374 | 0.374 | 0.0019 |
| 8 | 0.373 | 0.375 | 0.378 | 0.369 | 0.37 | 0.373 | 0.0037 |
| 9 | 0.375 | 0.377 | 0.374 | 0.37 | 0.371 | 0.373 | 0.0029 |
| 10 | 0.362 | 0.365 | 0.366 | 0.369 | 0.362 | 0.365 | 0.0029 |
| 11 | 0.365 | 0.364 | 0.369 | 0.368 | 0.37 | 0.367 | 0.0026 |
| 12 | 0.375 | 0.374 | 0.369 | 0.378 | 0.37 | 0.373 | 0.0037 |
| 13 | 0.363 | 0.366 | 0.368 | 0.37 | 0.372 | 0.368 | 0.0035 |
| 14 | 0.362 | 0.362 | 0.362 | 0.371 | 0.364 | 0.364 | 0.0039 |
| 15 | 0.365 | 0.368 | 0.37 | 0.37 | 0.363 | 0.367 | 0.0031 |
| 16 | 0.362 | 0.365 | 0.366 | 0.364 | 0.369 | 0.365 | 0.0026 |
| 17 | 0.369 | 0.37 | 0.378 | 0.377 | 0.37 | 0.373 | 0.0043 |
| 18 | 0.37 | 0.37 | 0.365 | 0.372 | 0.374 | 0.370 | 0.0033 |
| 19 | 0.365 | 0.366 | 0.369 | 0.372 | 0.375 | 0.369 | 0.0042 |

| | Median | Max | Min | Median − Min | 3 * StDev | Mean − 3 * StDev |
|---|---|---|---|---|---|---|
| 1 | 0.367 | 0.373 | 0.362 | 0.005 | 0.0128 | 0.354 |
| 2 | 0.371 | 0.378 | 0.368 | 0.003 | 0.0126 | 0.358 |
| 3 | 0.366 | 0.370 | 0.363 | 0.003 | 0.0091 | 0.357 |
| 4 | 0.372 | 0.375 | 0.363 | 0.009 | 0.0148 | 0.357 |
| 5 | 0.365 | 0.368 | 0.363 | 0.002 | 0.0058 | 0.359 |
| 6 | 0.374 | 0.378 | 0.369 | 0.005 | 0.0098 | |
| 7 | 0.374 | 0.377 | 0.372 | 0.002 | 0.0056 | |
| 8 | 0.373 | 0.378 | 0.369 | 0.004 | 0.0110 | 0.362 |
| 9 | 0.374 | 0.377 | 0.370 | 0.004 | 0.0086 | |
| 10 | 0.365 | 0.369 | 0.362 | 0.003 | 0.0088 | 0.356 |
| 11 | 0.368 | 0.370 | 0.364 | 0.004 | 0.0078 | 0.360 |
| 12 | 0.374 | 0.378 | 0.369 | 0.005 | 0.0111 | |
| 13 | 0.368 | 0.372 | 0.363 | 0.005 | 0.0105 | 0.358 |
| 14 | 0.362 | 0.371 | 0.362 | 0.000 | 0.0117 | 0.350 |
| 15 | 0.368 | 0.370 | 0.363 | 0.005 | 0.0093 | 0.359 |
| 16 | 0.365 | 0.369 | 0.362 | 0.003 | 0.0078 | 0.357 |
| 17 | 0.370 | 0.378 | 0.369 | 0.001 | 0.0130 | 0.357 |

TABLE 5-continued

Summary of the statistics of a UT internal inspection of the tank floor for an 82.5-ft diameter, 1,040,000-gal AST that is over 34 years old.

| 18 | 0.370 | 0.374 | 0.365 | 0.005 | 0.0100 | 0.360 |
|---|---|---|---|---|---|---|
| 19 | 0.369 | 0.375 | 0.365 | 0.004 | 0.0125 | 0.357 |

|  |  |  |  |  | Mean |
|---|---|---|---|---|---|

| | | | | | |
|---|---|---|---|---|---|
| Mean | 0.368 | 0.369 | 0.369 | 0.371 | 0.370 | 0.369 |
| StDev | 0.00545 | 0.00494 | 0.00504 | 0.00352 | 0.00375 | 0.00344 |
| Median | 0.366 | 0.368 | 0.369 | 0.370 | 0.370 | 0.369 |
| Max | 0.375 | 0.378 | 0.378 | 0.378 | 0.375 | 0.374 |
| Min | 0.362 | 0.362 | 0.362 | 0.364 | 0.362 | 0.364 |
| N | 19 | 19 | 19 | 19 | 19 | 19 |
| Mean − 3 * StDev | 0.352 | 0.354 | 0.354 | 0.360 | 0.359 | 0.359 |

|  | StDev | Median | Max | Min | Diff |
|---|---|---|---|---|---|
| Mean | 0.0034 | 0.369 | 0.374 | 0.365 | 0.004 |
| StDev | 0.0008 | 0.00368 | 0.00370 | 0.00334 | 0.00193 |
| Median | 0.0033 | 0.369 | 0.374 | 0.364 | 0.004 |
| Max | 0.0049 | 0.374 | 0.378 | 0.372 | 0.009 |
| Min | 0.0019 | 0.362 | 0.368 | 0.362 | 0.000 |
| N | 19 | 19 | 19 | 19 | 19 |
| Mean − 3 * StDev | | | | | |

The tables below summarize the types of tests and the potential Extension Time Interval in years if one or more of the tests are performed and passed. Table 6 summarizes the methods proposed are (1) a third-party approved leak detection test for like Vista's LRDP mass-based system; (2) ultrasonic (UT) measurements of floor thickness (0.001 in.); (3) a previous API inspection with UT and magnetic flux thickness measurements across the entire tank floor; and (4) an acoustic emission (AE) test for assessing active corrosion across the tank floor. A leak detection test can also be performed with the AE system. Its value is to confirm the approved test and to help interpret the AE corrosion measurements. The Extension Time Interval determined from the measurement program is dependent on the results. Only results a Pass leak detection test is shown. If the tank fails a leak detection test, it should be taken out of service and repair after confirming the presence of a leak.

TABLE 6

In-Service Tank Inspection Method for Prioritizing Out-of-Service Inspections

| Inspection Method | 3rd Party Approved Leak Detection Test | UT Thickness at One Location | API 653/ STI SP001 | AE Corrosion/ Leak Detection | Extension Time Interval (Years) |
|---|---|---|---|---|---|
| 1 | Yes | | | | 1 |
| 2 | Yes | | Yes | | 1 or more to 3 or 4 |
| 3 | Yes | | | Yes | 1 or more to 4 |
| 4 | Yes | Yes | | | 1 or more to 3 |
| 5 | Yes | Yes | Yes | | 2 to 5 |
| 6 | Yes | Yes | | Yes | 1 to 4 |
| 7 | Yes | Yes | Yes | Yes | 2 or 3 to 5 |

It is difficult to make a general statement about the number of years an out-of-service, internal inspection can be extended because it is heavily dependent on the results of the floor thickness estimates. Obviously, a tank floor that has a low rate of corrosion and greatly exceeds the minimum thickness will have a longer extension time than one that is experiencing a high rate of corrosion and is barely meeting the minimum thickness standard. Since all of the measurements made are trying to estimate the condition of the tank from limited data (as compared to a full, out-of-service, internal inspection, it is important to consider the degree of confidence in the spatial estimate of corrosion.

Table 7 illustrates the range of Extension Time Intervals that might be expected for various methods of the current invention for low to moderate corrosion rates. A more detail estimate for 203 implementations is illustrated below. If the rate of corrosion is high, then the Extension Time Interval would be shorted than those proposed in Table 2.

TABLE 7

In-Service Tank Inspection Method for Prioritizing Out-of-Service Inspections for Low to Moderate Corrosion Rates Unless Otherwise Specified

| Inspection Method | 3rd Party Approved Leak Detection Test | UT Thickness at One Location* | API 653/ STI SP001* | AE Corrosion/ Leak Detection | Extension Time Interval (Years) |
|---|---|---|---|---|---|
| 1 | Pass | | | | 1 |
| 2 | Pass | Floor > 0.1 in. | | | 2 |

TABLE 7-continued

In-Service Tank Inspection Method for Prioritizing Out-of-Service Inspections for Low to Moderate Corrosion Rates Unless Otherwise Specified

| Inspection Method | 3rd Party Approved Leak Detection Test | UT Thickness at One Location* | API 653/ STI SP001* | AE Corrosion/ Leak Detection | Extension Time Interval (Years) |
|---|---|---|---|---|---|
| 3a | Pass | | | A, B, C, FU½ | 4 or 5** |
| 3b | Pass | | | D, FU3 | 1 or 2** |
| 4 | Pass | >0.1 in. | | | 2 or 3** |
| 5 | Pass | >0.1 in. | Floor > 0.1 in. | | 4 or 5** |
| 6a | Pass | >0.1 in. | | A, B, C, FU½ | 4 or 5** |
| 7a | Pass | >0.1 in. | Floor > 0.1 in. | A, B, C, FU½ | 5 |
| 6b | Pass | >0.1 in. | | D, FU3 | 1 or 2** |
| 7b | Pass | >0.1 in. | Floor > 0.1 in. | D, FU3 | 2** |
| 5 | Pass | >0.1 in. | | E, FU4 | 0 |
| 6 | Pass | >0.1 in. | Floor > 0.1 in. | E, FU4 | 1 |

*Thickness is forecast out to Extension Time Interval based on max corrosion Rate
**Use the longer year extension if all thickness measurements are safely greater than 0.1 in.

As noted above, the AE test results are reported as either A through E or FU1 through FU4, where E and FU4 are expected to have significant damage, need significant repair, and have a high probability of leaking. A grade of C means no damage or repair required, but some maintenance is needed. A grade of FU3 has more damage than C, but is not likely to be leaking.

The proposed method and apparatuses of the present invention are best used as part of a risk-based inspection procedure, where these measurements can provide a substantive basis for risk mitigation.

The method of the present invention for estimating the Extension Time Interval is based on a Bayesian statistical analysis. There are a variety of probability hypothesis statements that can be made that are essentially equivalent. One example is: "What's the probability that that there is adequate thickness in the floor of a tank to extend the time between inspections (a given time interval) given that we have conducted and passed a leak detection test?" If we assume that adequate floor thickness is 0.1 in. (0.05 in. for tanks with secondary containment), we can state this probability statement as, "What's the probability that that the thickness in the floor of a tank is greater than 0.1 in. (0.05 in.) so that the time between inspections can be extended (a given time interval) given that we have conducted and passed a leak detection test?" Another way of stating the hypothesis is "What's the probability that that the time between inspections (a given time interval) given that we have conducted and passed a leak detection test and there is adequate thickness in the floor of a tank?" In line with the assumption above, this hypothesis can be stated as "What's the probability that that the time between inspections (a given time interval) given that we have conducted and passed a leak detection test and the thickness of the floor of a tank is greater than 0.01 in. (0.05 in.)?" All of these statements can be made more complex by adding additional a priori information. For example, "What's the probability that that the time between inspections (a given time interval) given that (1) we have conducted and passed a leak detection test, (2) there is adequate thickness in the floor of a tank, and (3) the corrosion of the tank floor is low?," or GIVEN that (1), (2), (3), and (4) . . . (n). We can also expand (2) to include additional sensors like those illustrated below in (2a) through (2e). We can add a minimum acceptable floor thickness in (3) like 0.1 in. (0.05 in. for secondarily contained tanks). We can also add state conditions like (4) low corrosion rates, (5) consistency between methods and data collected.

(2a) Local UT thickness measurements,
(2b) Previous Out-of-Service Floor Thickness Measurements over the nominal thickness at the Initial Installation,
(2c) Previous Out-of-Service Floor Thickness Measurements over Previous Out-of-Service Inspection,
(2d) An AE Corrosion Activity Measurement and a Previous Out-of-Service Inspection,
(2e) An AE Corrosion Activity Measurement where the corrosion rate throughout the tank is low and the previous evaluation of the floor thickness throughout the entire tank floor is more than adequate (i.e., >>the minimum acceptable thickness (e.g., close to the original thickness of the tank floor).

The probability hypothesis can be very complicated. The heart of the Extension Time Interval is a Passing Leak Detection Test and an estimate of the minimum thickness of the tank floor that exceeds 0.1 in. (or 0.05 in.) throughout the extension period. There is a level of uncertainty on this thickness estimate depending on the number of sensors, when the in-tank measurements were made, and what the spatial distribution of the floor thickness is. Thus, a tank with hot spots or local areas of high corrosion would have a shorter Extension Time Interval than a tank with uniform corrosion, knowledge of the spatial distribution of floor thickness, and an up-to-date estimate of floor thickness. It is because of this uncertainty that longer Extension Time Intervals than 4 or 5 years is not recommended.

For the preferred method of the present invention, the probability hypothesis would be, "What's the probability that that the thickness in the floor of a tank is greater than 0.1 in. (0.05 in.) so that the time between inspections can be extended a certain time interval (to be specified as a function of the sensor measurements and sensor measurement results) given that (1) we have conducted and passed a leak detection test, (2) we have made several measurements of the local tank floor thickness, (3) we have made an estimate of the spatial distribution of floor thickness and corrosion rate with one or more methods, (4) the thickness and rate of corrosion are Low, Moderate, or High, (5) the floor thickness estimates are correlated and consistent with each other, and (6) the most current in-tank measurements of floor thickness (e.g., a UT sensor) or corrosion activity (e.g., an AE system) and whether or not the thickness and/or corrosion rate/activity are correlated with, consistent with, and/or smaller than the estimates made during previous out-of-service inspection?" For simplicity, we can start with only tanks that have Passed a Leak Detection Test and will result in a minimum floor thickness that is adequate or greater than 0.1 in. We can further combine the thickness measurements (items (2) and (3) from the results of the measurement (items (4)-(6)).

As stated above, we can break the probability statement into many parts as a complex statement, or simply combine it into a succinct statement as presented in the illustration below. Typically, one would assign a probability to Bayes Theorem, but one can also use a Confidence Level (from 0 to 10) to describe the Method and Results, and then associate an Extension Time Interval (0 to 5 Years) with each Confidence Level. This is described below.

A simple illustration of the application of this method is presented below. The following hypothesis is tested. What's the probability that the thickness in the floor of a tank is of adequate thickness (i.e., greater than 0.1 (or 0.05 in. for tanks that are secondarily contained)) so that the time interval between inspections can to be safely extended by a certain time interval GIVEN that the tank passes a leak detection test." We consider a Passing Test with third-party evaluated LD Test Method with a $P_D \geq 95\%$ and $P_{FA} \leq 5\%$. A Passing Test indicates that there is a high probability that there are no holes in the tank floor or no holes in the tank floor that are large enough to actually leak due to debris closing the hole or no holes in the tank floor that detected as leaking. For purposes of this illustration, we consider the five different measurement of floor thickness described above in (2a) through (2 e) that will support the notion of adequate floor thickness or some pre-determined minimum, desirable floor thickness, i.e., P(W). For this illustration, P(W) incorporates the thickness inferences from one or more of the measurement methods of the present invention. For this illustration, we will assume 0.1 in. (and 0.05 in.).

Mathematically, Bayes' theorem gives the relationship between the probabilities of W and Q, P(W) and P(Q), and the conditional probabilities of Q given W and W given Q, P(Q|W) and P(W|Q). In its most common form, it is:

$$P(W/Q) = \frac{P(Q/W)P(W)}{P(Q)}$$

where this probability statement can also be expressed as $$P(W/Q) = \frac{P(Q/W)P(W)}{P(Q/W)P(W) + P(Q/M)P(M)}$$

or $$P(W/Q) = \frac{P(Q/W > a)P(W > a)}{P(Q/W > 0)P(W > a) + P(Q/M < a)P(M < a)}$$

where

W=adequate floor thickness or FT>a, where "a" may be 0.0 in. or 0.1 or 0.05 in. or some acceptable thickness, which is estimated from one or more of the five current and previous measurements of the tank floor thickness or tank floor corrosion for this illustration.

Q=Pass a leak detection test with a known $P_D$, LR, and $P_{FA}$

P(Q) is the probability of Passing a Leak Detection Test. We normally define P(Q) for a Leak Rate (i.e., Hole Size) and perform the test such that the probability of detection of a leak of a certain size is at least 95%. If the LR is smaller than the smallest hole that will leak, then this become the P(Q) for all leak rates. If not, then it is possible that a leak may still exist and be too small to detect with a high reliability. Also, a leak of a detectable size can be missed to because of the statistic nature of the test.

P(W)=Probability that the floor is of adequate thickness to extend the time interval between tests.

P(W/Q)=Probability that floor is of adequate thickness to extend the time interval between tests given that a Passing Leak Detection Test.

P(Q/W)=Probability of Passing a Leak Detection test given that the floor has adequate thickness.

$$P(Q/W > a)P(W > a) + P(Q/W < a)P(W < a)$$

$$P(W/Q) = \frac{P(Q/W > a)P(W > a)}{P(Q/W > a)P(W > a) + P(Q/W < a)P(W < a)}$$

$$= \frac{(95\%)(80\%)}{(95\%)(80\%) + (5\%)(20\%)} = 98.7\%$$

where the test was originally conducted with a probability of passing of 95%. While 95% is very good, 98.7% is even better. The added reliability is provided by the a priori information about the expectations of conducting a test with information about the tank thickness. We have assumed the application of different measurement systems and incorporate one type of result, i.e., whether or not the measured corrosion rate is high or low.

Tables 8 and 9 below illustrate some results for different methods of the present invention. These results present the likelihood of a tank not failing or not leaking. We assume that a probability of 95% or 99% is generally acceptable to justify extending the time interval between inspections. The 99% probabilities are designated in red font and the 95% probabilities are designate in blue font. The 90% probabilities are deemed questionable and are highlighted in yellow. The 90% probabilities designate the maximum extension time that might be considered. More measurement data, such as spatial floor thickness data, would be required to justify an extension. Table 8 is for low corrosion rates, and Table 9 is for high corrosion rates. One can see that the time between inspections can be longer for tanks with low corrosion vice tanks with high corrosion rates.

TABLE 8

Illustration of the Number of Years that an Internal Inspection can be Extended for Methods where All of
the Sensors Indicate Low Corrosion and More than Adequate Floor Thickness at the End of the Inspection Interval Extension

| Methods<br>Low Corrosion Activity with<br>More than Adequate Thickness for Each Sensor | Low CR<br>Number of<br>Sensors/Tests | Probability of Extension Time Interval - Years | | | | | Decision<br>in Years |
|---|---|---|---|---|---|---|---|
| | | 1 | 2 | 3 | 4 | 5 | |
| Leak Detection Pass* | 1 | 95.0% | 70.0% | 60.0% | 50.0% | 50.0% | 1 |
| Leak Detection Pass & Local UT Floor Thickness | 2 | 99.0% | 95.0% | 90.0% | 70.0% | 60.0% | 2 to 3 |
| Leak Detection Pass & Previous Internal Floor Thickness Inspection | 2 | 99.0% | 95.0% | 90.0% | 70.0% | 60.0% | 2 to 3 |
| Leak Detection Pass & AE Corrosion Activity | 2 | 99.0% | 95.0% | 90.0% | 80.0% | 70.0% | 2 to 3 |
| Leak Detection Pass & Local UT & Previous Internal Floor Thickness Inspections | 3 | 99.0% | 99.0% | 99.0% | 95.0% | 90.0% | 4 to 5 |
| Leak Detection Pass & Local UT & AE Corrosion Activity | 3 | 99.0% | 99.0% | 95.0% | 90.0% | 90.0% | 3 to 4 |
| Leak Detection Pass & Local UT & Previous Internal & AE Corrosion Activity | 4 | 99.0% | 99.0% | 99.0% | 99.0% | 99.0% | 5 |

*Assumes some risk/probabilitic information about the tanks, tank history, and environment exist

TABLE 9

Illustration of the Number of Years that an Internal Inspection can be Extended for Methods where All of
the Sensors Indicate High Corrosion and Minimum Floor Thickness at the End of the Inspection Interval Extension

| Methods<br>High Corrosion Activity that<br>has Minimum Thickness for Each Sensor | High CR<br>Number of<br>Sensors/Tests | Probability of Extension Time Interval - Years | | | | | Decision<br>in Years |
|---|---|---|---|---|---|---|---|
| | | 1 | 2 | 3 | 4 | 5 | |
| Leak Detection Pass* | 1 | 95.0% | 70.0% | 60.0% | 50.0% | 50.0% | 1 |
| Leak Detection Pass & Local UT Floor Thickness | 2 | 99.0% | 90.0% | 70.0% | 60.0% | 50.0% | 1 to 2 |
| Leak Detection Pass & Previous Internal Floor Thickness Inspection | 2 | 99.0% | 90.0% | 80.0% | 80.0% | 70.0% | 1 to 2 |
| Leak Detection Pass & AE Corrosion Activity | 2 | 95.0% | 90.0% | 80.0% | 70.0% | 60.0% | 1 to 2 |
| Leak Detection Pass & Local UT & Previous Internal Floor Thickness Inspections | 3 | 99.0% | 95.0% | 90.0% | 70.0% | 60.0% | 2 to 3 |
| Leak Detection Pass & Local UT & AE Corrosion Activity | 3 | 99.0% | 90.0% | 70.0% | 60.0% | 50.0% | 1 to 2 |
| Leak Detection Pass & Local UT & Previous Internal & AE Corrosion Activity | 4 | 99.0% | 95.0% | 90.0% | 80.0% | 70.0% | 2 to 3 |

*Assumes some risk/probabilitic information about the tanks, tank history, and environment exist Powerful statements can be made depending on the type and the results of the Leak Detection and the Thickness Measurements. As described above, the study of the use of AE for determining the corrosion activity across the tank floor has generated some interesting statistics about the integrity status of the tank. The studies suggest that about ⅔ of the tanks studied are in really good shape and do not need maintenance or repair. Stated another way 2 out of 3 tanks are in good shape. Thus, this type of information can be taken into account when establishing the probabilities in Tables 8 and 9 and is the reason the probabilities did not drop below 50%.

A risk-based inspection needs to estimate both the likelihood of a failure and the consequence of the failure. We have made an estimate of the likelihood of that the tank will not leak and that the thickness of the tank floor will maintain a certain minimum thickness (0.1 in. or 0.05 in.) over the Extension Time Interval given that a certain suite of sensor measurement systems were used to generate the data as input to the decision making models and given that certain results were obtained with this sensor suite. If this assessment is inaccurate, then the tank may leak and/or the floor may corrode more than desired. The consequence of an inaccurate decision is the cost of characterizing and remediating the leak, the cost of repairing the tank floor, and the cost of lost operations while the tank is out of service. This latter can be the most significant cost and in a small facility where only 1 or 2 tanks can be used to store a specific type of product, the cost of lost operations can be even more significant. In addition to actual cost, there is a public image issue and potential health hazards. While there is a consequence to having an incident during the Extension Time Interval, there is also a cost to prematurely scheduling an internal inspection where none is required. There is no need to remove a tank from service for maintenance and/or repair when it is not needed. There is no need to lose operational services during this period. In fact, this often leads to more problems because an inspection may not be performed on a tank that really needs one because the decision making process is lacking information. Thus, there are multiple consequences, one for inspecting a tank when it is not really required, another for not inspecting a tank when it would benefit from the inspection, and final one for extending the time between inspections too long, allowing the possibility of an incident to occur. The former is not usually considered and should be, because it is a real expenditure of funds, funds that could be better used on tanks that could benefit more. The proposed method of the present invention helps prioritize and manage tank maintenance and repair operations. It allows the best use of available funds to maintain the tanks in a facility in the best operational shape.

The cost of performing an inspection can be estimated reasonably well. This is also true of the cost of lost operations. The cost of characterizing and remediating a leak is not as easy to estimate and is dependent on the size of the leak and the environmental and health damage resulting from the leak; the cost of lost operations is then a direct function of how long this takes to characterize and remediate the leak. The other costs (e.g., dealing with the public) are equally uncertain and depend up the severity of the incident. The probability of a large leak or a structural failure is relatively small and should be taken into account when estimating the consequence of a problem. Thus, if there is a probability of 3% of the tanks leaking in a facility and the estimated cost of to correct an incident is $3 M, the actual consequence is 3% of $3 M, or $90,000. In general, the cost saving of each inspection dwarfs this consequence cost (e.g., $300,000). While the cost of an incident can be an order of magnitude larger than an inspection if an incident occurs, the probability is low and for facilities with secondary containment, the consequences and the costs are even lower. Estimating the probability of a leak is difficult, and if it is unrealistically large or not taken into account at all (e.g., assuming a probability of a leak of 100%), then it can seriously bias the inspection process and increase the overall costs and increase the chance of an incident. Regardless, it is clear from any reasonable estimate that the consequences of not prioritizing and managing optimally will outweigh the consequence of a leak.

In its simplest application, we can assume the consequences apply equally for all tanks and all extension time intervals. This is probably a reasonable approach if the sensor suite used in the assessment is adequate and includes a passing leak detection test with a reliable method, an in-tank measurement of floor thickness and corrosion rate, and information about the spatial characteristics of the tank floor. If not, one can increase the probability of a leak as a function of the Extension Time Interval, i.e., the longer Extension Time, the higher the probability of a leak. Other things may increase the probability of a leak. For example, the probability may also be higher for tanks with a high rate of corrosion and the floor thickness forecast. In general, if the sensor suite is adequate and the minimum acceptable floor thickness of 0.1 in. (or 0.05 in. for secondarily contained tanks), then the probability of a leak is about the same for all tanks.

Table 10 illustrates the decision making process. If the probability of successfully extending the time interval 5 years between inspections is 95%, the present value of the cost savings of a $300,000 internal inspection is $366,314. If the probability of a leak is 3% for a method with a 99% probability of success, and the probability increases as the probability of success decreases, we can compare the cost savings to the cost. If the cost consequence of a leak exceeds the cost savings, then the method should not be used to extend the time interval. This model increases the probability of a leak for all method probabilities less than 95% by 1.25. Thus, the probability of a leak for a method with a 50% confidence level in the method, the probability of a leak to use in the computation is 1.25 times 6% (1.25*3%/(100%−50%)=7.5%).

TABLE 10

Decision Model Illustration with Cost Consequences included.

| | Confidence Level Per Likelihood | Extension Time in Years | Cost Savings Per Year | Probability of a Leak | Cost of a Leak | Cost Saving Consequence of Extension | Cost Consequence of a Leak | Should the Extension Time Be Extended |
|---|---|---|---|---|---|---|---|---|
| Inspection Method 1 | 99.0% | 5 | $300,000 | 3.00% | $3,000,000 | $366,314 | $270,000 | Yes |
| Inspection Method 2 | 95.0% | 5 | $300,000 | 3.16% | $3,000,000 | $366,314 | $284,211 | Yes |
| Inspection Method 1 | 90.0% | 5 | $300,000 | 4.17% | $3,000,000 | $366,314 | $375,000 | No |
| Inspection Method 1 | 80.0% | 5 | $300,000 | 4.69% | $3,000,000 | $366,314 | $421,875 | No |
| Inspection Method 1 | 70.0% | 5 | $300,000 | 5.36% | $3,000,000 | $366,314 | $482,143 | No |
| Inspection Method 1 | 60.0% | 5 | $300,000 | 6.25% | $3,000,000 | $366,314 | $562,500 | No |
| Inspection Method 1 | 50.0% | 5 | $300,000 | 7.50% | $3,000,000 | $366,314 | $675,000 | No |

In general, the decision about extension is best made assuming a confidence level of 99% or 95%, and it is assumed that the consequence for using a lesser method to base the extension period is too low to accept.

Tables 11 and 12 summarize a more comprehensive list of various types of Methods and the various types of types of Test Results to illustrate the methods summarized in Table 6 and Table 7, respectively. All of the methods assume that they have Passed a Leak Detection Test. Furthermore, all of the preferred methods have a high probability that the floor thickness will be greater than 0.1 in., or some acceptable minimum floor thickness, and that the corrosion rate is low to moderate, but not high, because of one or more in-tank floor measurements. The Extension Time Interval, described above in terms of Bayesian statistics, is selected on the basis of a Confidence Interval that the method will achieve a 95% or 99% probability of not leaking or structurally failing during the Extension Time Interval. In general, the probability is 99%, except where two or more levels of confidence are expressed and the lower probability is assigned. Table 13 summarizes the Confidence Levels estimated for each method and the Extension Time Interval in years.

TABLE 13

Summary of Confidence Levels on Different
Methods and the Recommended Extension Times

| Overall Confidence of Integrity Assessment | Extension Time Interval (Years) |
|---|---|
| 0 | 0 |
| 1 | 0 |
| 2 | 1 |
| 3 | 2 |
| 4 | 2 |
| 5 | 2 |
| 6 | 3 |
| 7 | 3 |
| 8 | 4 |
| 9 | 5 |
| 10 | 5 |

The Confidence Intervals were assessed in terms of Low, Moderate, and High rates of corrosion rates for the local UT thickness measurements, the previous Out-of-Service Floor Thickness Measurements, and the AE corrosion activity, whether or not the minimum thickness of the tank floor will be exceeded before the Extension Time Interval as assessed by the UT local measurements and the previous Out-of-Service floor inspection measurements, whether or not the UT measurements are correlated and are consistent with these three floor thickness and/or corrosion measurements, whether or not the UT local thickness and corrosion rate measurements are smaller/larger than the Out-of-Service floor thickness and corrosion rate measurements, and whether or not the leak detection results of the AE system are consistent with the results of the Leak Detection test.

In general, almost all of the various methods include local in-tank measurements of the floor thickness so that an estimate of the maximum general or uniform corrosion rate and minimum floor thickness can be determined for the whole tank and to use it in estimating the spatial distribution of the corrosion rate and floor thickness if the floor corrodes evenly. The local measurement of floor thickness is very powerful, because it is a direct indication of the floor thickness made at the time in which the extension time interval is made.

As illustrated in Tables 7 and 8 and 11 and 12, the Methods that permit greater than a 1-year extension all include a Leak Detection Test and at least one other in-tank measurement of the tank floor thickness. A 1-year extension is permitted if only a Leak Detection Test is Passed with an EPA-approved test method providing the corrosion activity of the tank is known to be Low. Given the ease and low incremental cost of making one-or more local measurements of the floor thickness with an in-tank UT sensor, it is unlikely that only a Leak Detection Test will be performed. Thus, it is easy to verify the corrosion activity for a 1-year extension and with adequate floor thickness, more than a 1-year extension is possible. The Methods that permit the longest extension times all include a measurements that allows a quantitative estimate of the spatial distribution of corrosion potential of the floor. Up to 5 years is possible.

Table 14 sorts the methods in Table 11 so that the methods with the highest Confidence Intervals and the longest Extension Time Intervals are at the top of the table. Table 15 summarizes a composite interpretation of the Extension Methods. The Extension Time Intervals with the longest extension times involves the use of multiple sensor measurements and low to moderate corrosion rates. All the methods illustrated here have required that the floor thickness at the end of the Extension Time Interval meet the 0.1 in. or 0.05 in. minimum thickness. This does not need to be the case, but it is for all of the illustrated methods because it gives a high level of confidence. It is important to note that unless the tank is taken out-of-service and a full inspection like the ones following API 653, API 12R, or STI SP001, the thickness estimated using the methods of the present invention are all estimates without complete information of the actual spatial distribution of floor thickness.

The number of methods and the summary of the methods is presented in Table 15. The methods with the longest Extension Time involve the use of a "Passing" Leak Detection Test and at least 2 other measurements of floor thickness, where one of those measurements is almost always a local floor thickness measurement with a UT sensor (i.e., 2 to 5 years). The longest Extension Times occur for the tanks with the lowest rates of corrosion (and highest floor thickness). While it would be preferred that the local UT measurements of floor thickness be correlated and consistent with and lower than the previous API 653 inspection, the results do not support this premise. However, the results indicate that such correlation and consistency is required when using the AE corrosion activity method, because actual measurements of floor thickness are not made. For each Extension Time Interval, there is generally two levels of confidence. Methods with the highest level of confidence are preferred. The higher level of confidence is generally associated with the lower rates of corrosion.

TABLE 15

Summary of the Extension Time Interval and Confidence Level for 203 Different Measurement Methods and Test Results

| Methods 4 Sensors (1 LD + 3 Floor) | Methods 4 Sensors (1 LD + 2 Floor) | Methods 4 Sensors (1 LD + 1 Floor) | Methods 4 Sensors (1 LD + 0 Floor) | Number of Methods | % of Methods | Leak Detection Method | UT Local Measurement Corrosion Rate | | API 653 Tank Floor Thickness Corrosion Rate |
|---|---|---|---|---|---|---|---|---|---|
| 65.0% | 35.0% | 0.0% | 0.0% | 20 | 9.9% | PASS | Low, Moderate | >, < | Low, Moderate |
| 63.2% | 36.8% | 0.0% | 0.0% | 19 | 9.4% | PASS | Low, Moderate | >, < | Low, Moderate |
| 77.3% | 22.7% | 0.0% | 0.0% | 44 | 21.7% | PASS | Low, Moderate | >, < | Low, Moderate |
| 65.2% | 26.1% | 8.7% | 0.0% | 69 | 34.0% | PASS | Low, Moderate, High | >, < | Low, Moderate, High |
| 52.6% | 42.1% | 5.3% | 0.0% | 19 | 9.4% | PASS | Moderate High | >, < | Moderate High |

TABLE 15-continued

Summary of the Extension Time Interval and Confidence Level for 203 Different Measurement Methods and Test Results

| 59.4% | 21.9% | 9.4% | 9.4% | 32 | 15.8% | PASS | Moderate High | >, < | Moderate High |
|---|---|---|---|---|---|---|---|---|---|
| | UT Local Correlated with API 653 Corrosion Rate | AE Corrosion Activity | UT Local Correlated with AE Corrosion | AE Correlated Leak Detection | UT Min Thickness >0.1, 0.05 in. Over ETI | API 653 Min Thickness > 0.1, 0.05 in. Over ETI | Overall Confidence of Integrity Assessment | | Extension Time Interval (Years) UT > OOSI &/OR AE PASS |
| | No, Yes | Low, Moderate | Yes | Yes | Yes | Yes | 9, 10 | | 5 |
| | No, Yes | Low, Moderate | Yes, Some No | Yes | Yes | Yes | 8 | | 4 |
| | No, Yes | Low, Moderate | Yes, Some No | Yes, Some No | Yes | Yes, Some No | 6, 7 | | 3 |
| | No, Yes | Low, Moderate, High | Yes, Some No | Yes, Some No | Yes | Yes, Some No | 3, 4 | | 2 |
| | No, Yes | Moderate High | Yes | Yes | Yes | Yes | 2, 3 | | 1 |
| | No, Yes | High | Yes, Some No | Yes, Some No | Yes | Yes, Some No | 0, 1 | | 0 |

About 20% (19.3%) of the methods illustrating the present invention would permit an Extension Time Interval of 4 or 5 years, and about 16% (15.8%) would not permit any extension and require an out-of-service inspection. About 55% (55.7%) of the methods would permit a 2- or 3-year extension with 10% (9.4%) allowing only a 1-year extension. Thus, 75% (74.8%) of the methods illustrating the present invention would allow a 2 to 5 year extension in the time interval between out-of-service inspections.

The methods and apparatuses of the present invention can include other measurement sensors and different combinations of such sensors. For example, a long range ultrasonic test (LRUT) might be used on the outside shell of the tank vice a previous out-of-service inspection or a AE corrosion activity measurement. In contrast to these two methods, this type of LRUT measurement only measures the tank floor condition in the outer 1.2 m or so of the tank floor, but this LRUT measurement is a measurement of floor thickness and the current floor thickness, where the other methods are not. Also, this LRUT measurement also measures the floor thickness in the area where the tank floor is likely to corrode the most. The confidence levels and the Extension Time Intervals would then change if this LRUT method were to replace the out-of-service inspection or the AE corrosion method. The preferred method of the present invention is comprised of a compact, in-tank set of measurements.

TABLE 11

In-Service Tank Inspection Methods for Prioritizing Out-of-Service Inspections

| Method | Leak Detection Method | UT Local Measurement Corrosion Rate | API 653 Tank Floor Thickness Corrosion Rate | UT Local Correlated with API 653 Corrosion Rate | AE Corrosion Activity | UT Local Correlated with AE Corrosion | AE Correlated Leak Detection | UT Min Thickness >0.1, 0.05 in. Over ETI | API 653 Min Thickness >0.1, 0.05 in. Over ETI | Overall Confidence of Integrity Assessment | Extension Time Interval (Years) UT > OOSI &/OR AE PASS |
|---|---|---|---|---|---|---|---|---|---|---|---|
| | | | | Method 0 - Leak Detection Only | | | | | | | |
| | PASS | | | | | | | | | 2 | 1 |
| | FAIL | | | | | | | | | 0 | 0 |
| | | | | Method 1 - Leak Detection and Previous Out-of-Service Floor Inspection | | | | | | | |
| | PASS | Low | | | | | | Yes | | 5 | 2 |
| | PASS | Low | | | | | | No | | 0 | 0 |
| | PASS | Moderate | | | | | | Yes | | 4 | 2 |
| | PASS | Moderate | | | | | | No | | 0 | 0 |
| | PASS | High | | | | | | Yes | | 4 | 2 |
| | PASS | High | | | | | | No | | 0 | 0 |
| | | | | Method 2 - Leak Detection, UT Local Floor Thickness, and Previous Out-of-Service Floor Thickness | | | | | | | |
| 1 | PASS | | Low | | | | | | Yes | 5 | 2 |
| 2 | PASS | | Low | | | | | | No | 0 | 0 |
| 3 | PASS | | Moderate | | | | | | Yes | 4 | 2 |
| 4 | PASS | | Moderate | | | | | | No | 0 | 0 |
| 5 | PASS | | High | | | | | | Yes | 3 | 2 |
| 6 | PASS | | High | | | | | | No | 0 | 0 |

TABLE 11-continued

In-Service Tank Inspection Methods for Prioritizing Out-of-Service Inspections

| Method | Leak Detection Method | UT Local Measurement Corrosion Rate | API 653 Tank Floor Thickness Corrosion Rate | UT Local Correlated with API 653 Corrosion Rate | AE Corrosion Activity | UT Local Correlated with AE Corrosion | AE Correlated Leak Detection | UT Min Thickness >0.1, 0.05 in. Over ETI | API 653 Min Thickness >0.1, 0.05 in. Over ETI | Overall Confidence of Integrity Assessment | Extension Time Interval (Years) UT > OOSI &/OR AE PASS |
|---|---|---|---|---|---|---|---|---|---|---|---|
| Method 3 - Leak Detection, UT Local Floor Thickness, and Previous Out-of-Service Floor Thickness |||||||||||| 
| 1 | PASS | Low | > | Low | Yes | | | Yes | Yes | 9 | 5 |
| 2 | PASS | Low | > | Low | No | | | Yes | Yes | 8 | 4 |
| 3 | PASS | Moderate | > | Low | No | | | Yes | Yes | 8 | 4 |
| 4 | PASS | Moderate | > | Moderate | Yes | | | Yes | Yes | 9 | 5 |
| 5 | PASS | Moderate | > | Moderate | No | | | Yes | No | 7 | 3 |
| 6 | PASS | Moderate | > | High | Yes | | | Yes | Yes | 7 | 3 |
| 7 | PASS | Moderate | > | High | No | | | Yes | No | 2 | 1 |
| 8 | PASS | High | > | Moderate | Yes | | | Yes | Yes | 5 | 2 |
| 9 | PASS | High | > | Moderate | No | | | Yes | No | 2 | 1 |
| 10 | PASS | High | > | High | Yes | | | Yes | Yes | 5 | 2 |
| 11 | PASS | High | > | High | No | | | Yes | No | 1 | 0 |
| Method 4 - Leak-Detection, UT Local Floor Thickness, and Previous Out-of-Service Floor Thickness |||||||||||| 
| 1 | PASS | Low | < | Low | Yes | | | Yes | Yes | 10 | 5 |
| 2 | PASS | Low | ,< | Low | No | | | Yes | Yes | 9 | 5 |
| 3 | PASS | Moderate | < | Low | No | | | Yes | Yes | 9 | 5 |
| 4 | PASS | Moderate | < | Moderate | Yes | | | Yes | Yes | 10 | 5 |
| 5 | PASS | Moderate | < | Moderate | No | | | Yes | No | 8 | 4 |
| 6 | PASS | Moderate | < | High | Yes | | | Yes | Yes | 8 | 4 |
| 7 | PASS | Moderate | ,< | High | No | | | Yes | No | 3 | 2 |
| 8 | PASS | High | < | Moderate | Yes | | | Yes | Yes | 6 | 3 |
| 9 | PASS | High | < | Moderate | No | | | Yes | No | 3 | 2 |
| 10 | PASS | High | < | High | Yes | | | Yes | Yes | 6 | 3 |
| 11 | PASS | High | < | High | No | | | Yes | No | 2 | 1 |
| Method 5 - Leak Detection, UT Local Floor Thickness, and AE Corrosion Activity |||||||||||| 
| A | PASS | Low | | | Low | Yes | Yes | Yes | | 9 | 5 |
| B | PASS | Low | | | Moderate | Yes | Yes | Yes | | 8 | 4 |
| C | PASS | Low | | | High | Yes | Yes | Yes | | 5 | 2 |
| D | PASS | Moderate | | | Low | Yes | Yes | Yes | | 8 | 4 |
| E | PASS | Moderate | | | Moderate | Yes | Yes | Yes | | 8 | 4 |
| F | PASS | Moderate | | | High | Yes | Yes | Yes | | 5 | 2 |
| G | PASS | High | | | Low | Yes | Yes | Yes | | 7 | 3 |
| H | PASS | High | | | Moderate | Yes | Yes | Yes | | 5 | 2 |
| I | PASS | High | | | High | Yes | Yes | Yes | | 2 | 1 |
| Method 6 - Leak Detection, UT Local Floor Thickness, and AE Corrosion Activity |||||||||||| 
| J | PASS | Low | | | Low | No | Yes | Yes | | 7 | 3 |
| K | PASS | Low | | | Moderate | No | Yes | Yes | | 6 | 3 |
| L | PASS | Low | | | High | No | Yes | Yes | | 3 | 2 |
| M | PASS | Moderate | | | Low | No | Yes | Yes | | 6 | 3 |
| N | PASS | Moderate | | | Moderate | No | Yes | Yes | | 6 | 3 |
| O | PASS | Moderate | | | High | No | Yes | Yes | | 3 | 2 |
| P | PASS | High | | | Low | No | Yes | Yes | | 5 | 2 |
| Q | PASS | High | | | Moderate | No | Yes | Yes | | 3 | 2 |
| R | PASS | High | | | High | No | Yes | Yes | | 0 | 0 |
| Method 5a - Leak Detection, UT Local Floor Thickness, and AE Corrosion Activity |||||||||||| 
| A | PASS | Low | | | Low | Yes | No | Yes | | 6 | 3 |
| B | PASS | Low | | | Moderate | Yes | No | Yes | | 5 | 2 |
| C | PASS | Low | | | High | Yes | No | Yes | | 2 | 1 |
| D | PASS | Moderate | | | Low | Yes | No | Yes | | 5 | 2 |
| E | PASS | Moderate | | | Moderate | Yes | No | Yes | | 5 | 2 |
| F | PASS | Moderate | | | High | Yes | No | Yes | | 2 | 1 |
| G | PASS | High | | | Low | Yes | No | Yes | | 4 | 2 |
| H | PASS | High | | | Moderate | Yes | No | Yes | | 2 | 1 |
| I | PASS | High | | | High | Yes | No | Yes | | 0 | 0 |
| Method 6a - Leak Detection, UT Local Floor Thickness, and AE Corrosion Activity |||||||||||| 
| J | PASS | Low | | | Low | No | No | Yes | | 4 | 2 |
| K | PASS | Low | | | Moderate | No | No | Yes | | 3 | 2 |
| L | PASS | Low | | | High | No | No | Yes | | 0 | 0 |
| M | PASS | Moderate | | | Low | No | No | Yes | | 3 | 2 |
| N | PASS | Moderate | | | Moderate | No | No | Yes | | 3 | 2 |
| O | PASS | Moderate | | | High | No | No | Yes | | 0 | 0 |
| P | PASS | High | | | Low | No | No | Yes | | 2 | 1 |
| Q | PASS | High | | | Moderate | No | No | Yes | | 0 | 0 |
| R | PASS | High | | | High | No | No | Yes | | 0 | 0 |

TABLE 11-continued

In-Service Tank Inspection Methods for Prioritizing Out-of-Service Inspections

| Method | Leak Detection Method | UT Local Measurement Corrosion Rate | | API 653 Tank Floor Thickness Corrosion Rate | UT Local Correlated with API 653 Corrosion Rate | AE Corrosion Activity | UT Local Correlated with AE Corrosion | AE Correlated Leak Detection | UT Min Thickness >0.1, 0.05 in. Over ETI | API 653 Min Thickness >0.1, 0.05 in. Over ETI | Overall Confidence of Integrity Assessment | Extension Time Interval (Years) UT > OOSI &/OR AE PASS |
|---|---|---|---|---|---|---|---|---|---|---|---|---|
| | Method 7 - Leak Detection, UT Local Floor Thickness, Previous Out-of-Service Floor Thickness, and AE Corrosion Activity |
| 1 A | PASS | Low | > | Low | Yes | Low | Yes | Yes | Yes | Yes | 10 | 5 |
| 1 B | PASS | Low | > | Low | Yes | Moderate | Yes | Yes | Yes | Yes | 9 | 5 |
| 1 C | PASS | Low | > | Low | Yes | High | Yes | Yes | Yes | Yes | 5 | 2 |
| 2 A | PASS | Low | > | Low | No | Low | Yes | Yes | Yes | Yes | 9 | 5 |
| 2 B | PASS | Low | > | Low | No | Moderate | Yes | Yes | Yes | Yes | 8 | 4 |
| 2 C | PASS | Low | > | Low | No | High | Yes | Yes | Yes | Yes | 4 | 2 |
| 3 D | PASS | Moderate | > | Low | No | Low | Yes | Yes | Yes | Yes | 8 | 4 |
| 3 E | PASS | Moderate | > | Low | No | Moderate | Yes | Yes | Yes | Yes | 7 | 3 |
| 3 F | PASS | Moderate | > | Low | No | High | Yes | Yes | Yes | Yes | 3 | 2 |
| 4 D | PASS | Moderate | > | Moderate | Yes | Low | Yes | Yes | Yes | Yes | 9 | 5 |
| 4 E | PASS | Moderate | > | Moderate | Yes | Moderate | Yes | Yes | Yes | Yes | 8 | 4 |
| 4 F | PASS | Moderate | > | Moderate | Yes | High | Yes | Yes | Yes | Yes | 4 | 2 |
| 5 D | PASS | Moderate | > | Moderate | No | Low | Yes | Yes | Yes | No | 8 | 4 |
| 5 E | PASS | Moderate | > | Moderate | No | Moderate | Yes | Yes | Yes | No | 7 | 3 |
| 5 F | PASS | Moderate | > | Moderate | No | High | Yes | Yes | Yes | No | 3 | 2 |
| 6 G | PASS | Moderate | > | High | Yes | Low | Yes | No | Yes | Yes | 7 | 3 |
| 6 H | PASS | Moderate | > | High | Yes | Moderate | Yes | No | Yes | Yes | 6 | 3 |
| 6 F | PASS | Moderate | > | High | Yes | High | Yes | No | Yes | Yes | 2 | 1 |
| 7 G | PASS | Moderate | > | High | No | Low | Yes | No | Yes | No | 6 | 3 |
| 7 E | PASS | Moderate | > | High | No | Moderate | Yes | No | Yes | No | 5 | 2 |
| 7 F | PASS | Moderate | > | High | No | High | Yes | No | Yes | No | 1 | 0 |
| 8 D | PASS | High | > | Moderate | Yes | Low | Yes | Yes | Yes | Yes | 7 | 3 |
| 8 E | PASS | High | > | Moderate | Yes | Moderate | Yes | Yes | Yes | Yes | 6 | 3 |
| 8 F | PASS | High | > | Moderate | Yes | High | Yes | Yes | Yes | Yes | 2 | 1 |
| 9 D | PASS | High | > | Moderate | No | Low | Yes | No | Yes | No | 6 | 3 |
| 9 E | PASS | High | > | Moderate | No | Moderate | Yes | No | Yes | No | 5 | 2 |
| 9 F | PASS | High | > | Moderate | No | High | Yes | No | Yes | No | 1 | 0 |
| 10 G | PASS | High | > | High | Yes | Low | Yes | Yes | Yes | Yes | 6 | 3 |
| 10 H | PASS | High | > | High | Yes | Moderate | Yes | Yes | Yes | Yes | 5 | 2 |
| 10 I | PASS | High | > | High | Yes | High | Yes | Yes | Yes | Yes | 1 | 0 |
| 11 G | PASS | High | > | High | No | Low | Yes | Yes | Yes | No | 5 | 2 |
| 11 H | PASS | High | > | High | No | Moderate | Yes | Yes | Yes | No | 4 | 2 |
| 11 I | PASS | High | > | High | No | High | Yes | Yes | Yes | No | 0 | 0 |
| | Method 8 - Leak Detection, UT Local Floor Thickness, Previous Out-of-Service Floor Thickness, and AE Corrosion Activity |
| 1 J | PASS | Low | > | Low | Yes | Low | No | Yes | Yes | Yes | 8 | 4 |
| 1 K | PASS | Low | > | Low | Yes | Moderate | No | Yes | Yes | Yes | 7 | 3 |
| 1 L | PASS | Low | > | Low | Yes | High | No | Yes | Yes | Yes | 3 | 2 |
| 2 J | PASS | Low | > | Low | No | Low | No | Yes | Yes | Yes | 7 | 3 |
| 2 K | PASS | Low | > | Low | No | Moderate | No | Yes | Yes | Yes | 6 | 3 |
| 2 L | PASS | Low | > | Low | No | High | No | Yes | Yes | Yes | 2 | 1 |
| 3 M | PASS | Moderate | > | Low | No | Low | No | Yes | Yes | Yes | 6 | 3 |
| 3 N | PASS | Moderate | > | Low | No | Moderate | No | Yes | Yes | Yes | 5 | 2 |
| 3 O | PASS | Moderate | > | Low | No | High | No | Yes | Yes | Yes | 1 | 0 |
| 4 M | PASS | Moderate | > | Moderate | Yes | Low | No | Yes | Yes | Yes | 7 | 3 |
| 4 N | PASS | Moderate | > | Moderate | Yes | Moderate | No | Yes | Yes | Yes | 6 | 3 |
| 4 O | PASS | Moderate | > | Moderate | Yes | High | No | Yes | Yes | Yes | 2 | 1 |
| 5 M | PASS | Moderate | > | Moderate | No | Low | No | Yes | Yes | No | 6 | 3 |
| 5 N | PASS | Moderate | > | Moderate | No | Moderate | No | Yes | Yes | No | 5 | 2 |
| 5 D | PASS | Moderate | < | Moderate | No | Low | Yes | Yes | Yes | No | 9 | 5 |
| 5 E | PASS | Moderate | ,< | Moderate | No | Moderate | Yes | Yes | Yes | No | 8 | 4 |
| 5 F | PASS | Moderate | < | Moderate | No | High | Yes | Yes | Yes | No | 4 | 2 |
| 6 G | PASS | Moderate | < | High | Yes | Low | Yes | No | Yes | Yes | 8 | 4 |
| 6 H | PASS | Moderate | < | High | Yes | Moderate | Yes | No | Yes | Yes | 7 | 3 |
| 6 F | PASS | Moderate | ,< | High | Yes | High | Yes | No | Yes | Yes | 3 | 2 |
| 7 G | PASS | Moderate | < | High | No | Low | Yes | No | Yes | No | 7 | 3 |
| 7 E | PASS | Moderate | ,< | High | No | Moderate | Yes | No | Yes | No | 6 | 3 |
| 7 F | PASS | Moderate | < | High | No | High | Yes | No | Yes | No | 2 | 1 |
| 8 D | PASS | High | < | Moderate | Yes | Low | Yes | Yes | Yes | Yes | 8 | 4 |
| 8 E | PASS | High | < | Moderate | Yes | Moderate | Yes | Yes | Yes | Yes | 7 | 3 |
| 8 F | PASS | High | ,< | Moderate | Yes | High | Yes | Yes | Yes | Yes | 3 | 2 |
| 9 D | PASS | High | < | Moderate | No | Low | Yes | No | Yes | No | 7 | 3 |
| 9 E | PASS | High | ,< | Moderate | No | Moderate | Yes | No | Yes | No | 6 | 3 |
| 9 F | PASS | High | < | Moderate | No | High | Yes | No | Yes | No | 2 | 1 |
| 10 G | PASS | High | < | High | Yes | Low | Yes | Yes | Yes | Yes | 7 | 3 |
| 10 H | PASS | High | < | High | Yes | Moderate | Yes | Yes | Yes | Yes | 6 | 3 |
| 10 I | PASS | High | ,< | High | Yes | High | Yes | Yes | Yes | Yes | 2 | 1 |
| 11 G | PASS | High | < | High | No | Low | Yes | Yes | Yes | No | 6 | 3 |

TABLE 11-continued

In-Service Tank Inspection Methods for Prioritizing Out-of-Service Inspections

| Method | | Leak Detection Method | UT Local Measurement Corrosion Rate | | API 653 Tank Floor Thickness Corrosion Rate | UT Local Correlated with API 653 Corrosion Rate | AE Corrosion Activity | UT Local Correlated with AE Corrosion | AE Correlated Leak Detection | UT Min Thickness >0.1, 0.05 in. Over ETI | API 653 Min Thickness >0.1, 0.05 in. Over ETI | Overall Confidence of Integrity Assessment | Extension Time Interval (Years) UT > OOSI &/OR AE PASS |
|---|---|---|---|---|---|---|---|---|---|---|---|---|---|
| 11 | H | PASS | High | ,< | High | No | Moderate | Yes | Yes | Yes | No | 5 | 2 |
| 11 | I | PASS | High | < | High | No | High | Yes | Yes | Yes | No | 1 | 0 |
| Method 9 - Leak Detection, UT Local Floor Thickness, Previous Out-of-Service Floor Thickness, and AE Corrosion Activity | | | | | | | | | | | | | |
| 1 | A | PASS | Low | < | Low | Yes | Low | Yes | Yes | Yes | Yes | 10 | 5 |
| 1 | B | PASS | Low | ,< | Low | Yes | Moderate | Yes | Yes | Yes | Yes | 10 | 5 |
| 1 | C | PASS | Low | < | Low | Yes | High | Yes | Yes | Yes | Yes | 6 | 3 |
| 2 | A | PASS | Low | < | Low | No | Low | Yes | Yes | Yes | Yes | 10 | 5 |
| 2 | B | PASS | Low | < | Low | No | Moderate | Yes | Yes | Yes | Yes | 9 | 5 |
| 2 | C | PASS | Low | ,< | Low | No | High | Yes | Yes | Yes | Yes | 5 | 2 |
| 3 | D | PASS | Moderate | < | Low | No | Low | Yes | Yes | Yes | Yes | 9 | 5 |
| 3 | E | PASS | Moderate | ,< | Low | No | Moderate | Yes | Yes | Yes | Yes | 8 | 4 |
| 3 | F | PASS | Moderate | < | Low | No | High | Yes | Yes | Yes | Yes | 4 | 2 |
| 4 | D | PASS | Moderate | < | Moderate | Yes | Low | Yes | Yes | Yes | Yes | 10 | 5 |
| 4 | E | PASS | Moderate | < | Moderate | Yes | Moderate | Yes | Yes | Yes | Yes | 9 | 5 |
| 4 | F | PASS | Moderate | ,< | Moderate | Yes | High | Yes | Yes | Yes | Yes | 5 | 2 |
| 5 | D | PASS | Moderate | < | Moderate | No | Low | Yes | Yes | Yes | No | 9 | 5 |
| 5 | E | PASS | Moderate | ,< | Moderate | No | Moderate | Yes | Yes | Yes | No | 8 | 4 |
| 5 | F | PASS | Moderate | < | Moderate | No | High | Yes | Yes | Yes | No | 4 | 2 |
| 6 | G | PASS | Moderate | < | High | Yes | Low | Yes | No | Yes | Yes | 8 | 4 |
| 6 | H | PASS | Moderate | < | High | Yes | Moderate | Yes | No | Yes | Yes | 7 | 3 |
| 6 | F | PASS | Moderate | ,< | High | Yes | High | Yes | No | Yes | Yes | 3 | 2 |
| 7 | G | PASS | Moderate | < | High | No | Low | Yes | No | Yes | No | 7 | 3 |
| 7 | E | PASS | Moderate | ,< | High | No | Moderate | Yes | No | Yes | No | 6 | 3 |
| 7 | F | PASS | Moderate | < | High | No | High | Yes | No | Yes | No | 2 | 1 |
| 8 | D | PASS | High | < | Moderate | Yes | Low | Yes | Yes | Yes | Yes | 8 | 4 |
| 8 | E | PASS | High | < | Moderate | Yes | Moderate | Yes | Yes | Yes | Yes | 7 | 3 |
| 8 | F | PASS | High | ,< | Moderate | Yes | High | Yes | Yes | Yes | Yes | 3 | 2 |
| 9 | D | PASS | High | < | Moderate | No | Low | Yes | Yes | Yes | No | 7 | 3 |
| 9 | E | PASS | High | ,< | Moderate | No | Moderate | Yes | Yes | Yes | No | 6 | 3 |
| 9 | F | PASS | High | < | Moderate | No | High | Yes | Yes | Yes | No | 2 | 1 |
| 10 | G | PASS | High | < | High | Yes | Low | Yes | Yes | Yes | Yes | 7 | 3 |
| 10 | H | PASS | High | < | High | Yes | Moderate | Yes | Yes | Yes | Yes | 6 | 3 |
| 10 | I | PASS | High | ,< | High | Yes | High | Yes | Yes | Yes | Yes | 2 | 1 |
| 11 | G | PASS | High | < | High | No | Low | Yes | Yes | Yes | No | 6 | 3 |
| 11 | H | PASS | High | < | High | No | Moderate | Yes | Yes | Yes | No | 5 | 2 |
| 11 | I | PASS | High | ,< | High | No | High | Yes | Yes | Yes | No | 1 | 0 |
| Method 10 - Leak Detection, UT Local Floor Thickness, Previous Out-of-Service Floor Thickness, and AE Corrosion Activity | | | | | | | | | | | | | |
| 1 | J | PASS | Low | < | Low | Yes | Low | No | Yes | Yes | Yes | 9 | 5 |
| 1 | K | PASS | Low | ,< | Low | Yes | Moderate | No | Yes | Yes | Yes | 8 | 4 |
| 1 | L | PASS | Low | < | Low | Yes | High | No | Yes | Yes | Yes | 4 | 2 |
| 2 | J | PASS | Low | < | Low | No | Low | No | Yes | Yes | Yes | 8 | 4 |
| 2 | K | PASS | Low | < | Low | No | Moderate | No | Yes | Yes | Yes | 7 | 3 |
| 2 | L | PASS | Low | ,< | Low | No | High | No | Yes | Yes | Yes | 3 | 2 |
| 3 | M | PASS | Moderate | < | Low | No | Low | No | Yes | Yes | Yes | 7 | 3 |
| 3 | N | PASS | Moderate | ,< | Low | No | Moderate | No | Yes | Yes | Yes | 6 | 3 |
| 3 | O | PASS | Moderate | < | Low | No | High | No | Yes | Yes | Yes | 2 | 1 |
| 4 | M | PASS | Moderate | < | Moderate | Yes | Low | No | Yes | Yes | Yes | 8 | 4 |
| 4 | N | PASS | Moderate | < | Moderate | Yes | Moderate | No | Yes | Yes | Yes | 7 | 3 |
| 4 | O | PASS | Moderate | ,< | Moderate | Yes | High | No | Yes | Yes | Yes | 3 | 2 |
| 5 | M | PASS | Moderate | < | Moderate | No | Low | No | Yes | Yes | No | 7 | 3 |
| 5 | N | PASS | Moderate | ,< | Moderate | No | Moderate | No | Yes | Yes | No | 6 | 3 |
| 5 | O | PASS | Moderate | < | Moderate | No | High | No | Yes | Yes | No | 2 | 1 |
| 6 | P | PASS | Moderate | < | High | Yes | Low | No | No | Yes | Yes | 6 | 3 |
| 6 | Q | PASS | Moderate | < | High | Yes | Moderate | No | No | Yes | Yes | 5 | 2 |
| 6 | R | PASS | Moderate | ,< | High | Yes | High | No | No | Yes | Yes | 1 | 0 |
| 7 | P | PASS | Moderate | < | High | No | Low | No | No | Yes | No | 5 | 2 |
| 7 | Q | PASS | Moderate | ,< | High | No | Moderate | No | No | Yes | No | 4 | 2 |
| 7 | R | PASS | Moderate | < | High | No | High | No | No | Yes | No | 1 | 0 |
| 8 | M | PASS | High | < | Moderate | Yes | Low | No | Yes | Yes | Yes | 6 | 3 |
| 8 | N | PASS | High | < | Moderate | Yes | Moderate | No | Yes | Yes | Yes | 5 | 2 |
| 8 | O | PASS | High | ,< | Moderate | Yes | High | No | Yes | Yes | Yes | 1 | 0 |
| 9 | M | PASS | High | < | Moderate | No | Low | No | No | Yes | No | 5 | 2 |
| 9 | N | PASS | High | ,< | ,Moderate | No | Moderate | No | No | Yes | No | 4 | 2 |
| 9 | O | PASS | High | < | Moderate | No | High | No | No | Yes | No | 1 | 0 |
| 10 | P | PASS | High | < | High | Yes | Low | No | Yes | Yes | Yes | 5 | 2 |
| 10 | Q | PASS | High | < | High | Yes | Moderate | No | Yes | Yes | Yes | 4 | 2 |
| 10 | R | PASS | High | ,< | High | Yes | High | No | Yes | Yes | Yes | 1 | 0 |
| 11 | P | PASS | High | < | High | No | Low | No | Yes | Yes | No | 4 | 2 |

TABLE 11-continued

In-Service Tank Inspection Methods for Prioritizing Out-of-Service Inspections

| Method | | Leak Detection Method | UT Local Measurement Corrosion Rate | API 653 Tank Floor Thickness Corrosion Rate | UT Local Correlated with API 653 Corrosion Rate | AE Corrosion Activity | UT Local Correlated with AE Corrosion | AE Correlated Leak Detection | UT Min Thickness >0.1, 0.05 in. Over ETI | API 653 Min Thickness >0.1, 0.05 in. Over ETI | Overall Confidence of Integrity Assessment | Extension Time Interval (Years) UT > OOSI &/OR AE PASS |
|---|---|---|---|---|---|---|---|---|---|---|---|---|
| 11 | Q | PASS | High | ,< | High | No | Moderate | No | Yes | Yes | No | 3 | 2 |
| 11 | R | PASS | High | < | High | No | High | No | Yes | Yes | No | 1 | 0 |

TABLE 12

In-Service Tank Inspection Methods for Prioritizing Out-of-Service Inspections

| Extension Time Interval (Years) 2 UT > OOSI & AE Leak Method 7 | Extension Time Interval (Years) 2 UT > OOSI & AE Leak Method 8 | Extension Time Interval (Years) 3 UT < OOSI & AE PASS Method 9 | Extension Time Interval (Years) 4 UT < OOSI & AE Leak Method 10 |
|---|---|---|---|
| 5 | 4 | 5 | 5 |
| 5 | 3 | 5 | 4 |
| 2 | 2 | 3 | 2 |
| 5 | 3 | 5 | 4 |
| 4 | 3 | 5 | 3 |
| 2 | 1 | 2 | 2 |
| 4 | 3 | 5 | 3 |
| 3 | 2 | 4 | 3 |
| 2 | 0 | 2 | 1 |
| 5 | 3 | 5 | 4 |
| 4 | 3 | 5 | 3 |
| 2 | 1 | 2 | 2 |
| 4 | 3 | 5 | 3 |
| 3 | 2 | 4 | 3 |
| 2 | 0 | 2 | 1 |
| 3 | 2 | 4 | 3 |
| 3 | 2 | 3 | 2 |
| 1 | 0 | 2 | 0 |
| 3 | 2 | 3 | 2 |
| 2 | 2 | 3 | 2 |
| 0 | 0 | 1 | 0 |

| | | | | |
|---|---|---|---|---|
| Number | 33 | 33 | 33 | 33 |
| Sum | 85 | 56 | 103 | 69 |
| Mean | 2.576 | 1.697 | 3.121 | 2.091 |
| Median | 3.000 | 2.000 | 3.000 | 2.000 |
| St Dev | 1.458 | 1.159 | 1.409 | 1.308 |
| Min | 0.000 | 0.000 | 0.000 | 0.000 |
| Max | 5.000 | 4.000 | 5.000 | 5.000 |

TABLE 14

| Method | | Method 1 | Method | Leak Detection Method | UT Local Measurement Corrosion Rate | API 653 Tank Floor Thickness Corrosion Rate | UT Local Correlated with API 653 Corrosion Rate | AE Corrosion Activity | UT Local Correlated with AE Corrosion | AE Correlated Leak Detection | UT Min Thickness >0.1, 0.05 in. Over ETI | API 653 Min Thickness >0.1, 0.05 in. Over ETI | Overall Confidence of Integrity Assessment | Extension Time Interval (Years) UT > OOSI &/OR AE PASS |
|---|---|---|---|---|---|---|---|---|---|---|---|---|---|---|
| Method 4 | 31 | 1 | | PASS | Low | | < | Low | Yes | | | | Yes | Yes | 10 | 5 |
| Method 7 | 92 | 1 A | | PASS | Low | | > | Low | Yes | Low | Yes | Yes | Yes | Yes | 10 | 5 |
| Method 9 | 180 | 1 A | | PASS | Low | | < | Low | Yes | Low | Yes | Yes | Yes | Yes | 10 | 5 |
| Method 9 | 181 | 1 B | | PASS | Low | | ,< | Low | Yes | Moderate | Yes | Yes | Yes | Yes | 10 | 5 |
| Method 9 | 184 | 2 A | | PASS | Low | | < | Low | No | Low | Yes | Yes | Yes | Yes | 10 | 5 |
| Method 4 | 34 | 4 | | PASS | Moderate | | < | Moderate | Yes | | | | Yes | Yes | 10 | 5 |
| Method 9 | 192 | 4 D | | PASS | Moderate | | < | Moderate | Yes | Low | Yes | Yes | Yes | Yes | 10 | 5 |
| Method 3 | 19 | 1 | | PASS | Low | | > | Low | Yes | | | | Yes | Yes | 9 | 5 |
| Method 4 | 32 | 2 | | PASS | Low | | ,< | Low | No | | | | Yes | Yes | 9 | 5 |
| Method 7 | 93 | 1 B | | PASS | Low | | > | Low | Yes | Moderate | Yes | Yes | Yes | Yes | 9 | 5 |
| Method 7 | 96 | 2 A | | PASS | Low | | > | Low | No | Low | Yes | Yes | Yes | Yes | 9 | 5 |
| Method 9 | 185 | 2 B | | PASS | Low | | < | Low | No | Moderate | Yes | Yes | Yes | Yes | 9 | 5 |
| Method 10 | 224 | 1 J | | PASS | Low | | < | Low | Yes | Low | No | Yes | Yes | Yes | 9 | 5 |
| Method 5 | 43 | A | | PASS | Low | | | | | Low | Yes | Yes | Yes | | 9 | 5 |
| Method 4 | 33 | 3 | | PASS | Moderate | | < | Low | No | | | | Yes | Yes | 9 | 5 |
| Method 9 | 188 | 3 D | | PASS | Moderate | | < | Low | No | Low | Yes | Yes | Yes | Yes | 9 | 5 |
| Method 3 | 22 | 4 | | PASS | Moderate | | > | Moderate | Yes | | | | Yes | Yes | 9 | 5 |
| Method 7 | 104 | 4 D | | PASS | Moderate | | > | Moderate | Yes | Low | Yes | Yes | Yes | Yes | 9 | 5 |

TABLE 14-continued

| Method | 1 | Meth-od | Leak Detec-tion Meth-od | UT Local Measure-ment Corrosion Rate | | API 653 Tank Floor Thickness Corrosion Rate | UT Local Correlated with API 653 Corrosion Rate | AE Corro-sion Activity | UT Local Corre-lated with AE Corro-sion | AE Corre-lated Leak Detec-tion | UT Min Thick-ness >0.1, 0.05 in. Over ETI | API 653 Min Thickness >0.1, 0.05 in. Over ETI | Overall Confi-dence of Integrity Assess-ment | Extension Time Interval (Years) UT > OOSI &/OR AE PASS |
|---|---|---|---|---|---|---|---|---|---|---|---|---|---|---|
| Method 9 | 193 | 4 E | PASS | Moderate | < | Moderate | Yes | Moderate | Yes | Yes | Yes | Yes | 9 | 5 |
| Method 9 | 196 | 5 D | PASS | Moderate | < | Moderate | No | Low | Yes | Yes | Yes | No | 9 | 5 |
| Method 3 | 20 | 2 | PASS | Low | > | Low | No | | | | Yes | Yes | 8 | 4 |
| Method 7 | 97 | 2 B | PASS | Low | > | Low | No | Moderate | Yes | Yes | Yes | Yes | 8 | 4 |
| Method 8 | 136 | 1 J | PASS | Low | > | Low | Yes | Low | No | Yes | Yes | Yes | 8 | 4 |
| Method 10 | 225 | 1 K | PASS | Low | ,< | Low | Yes | Moderate | No | Yes | Yes | Yes | 8 | 4 |
| Method 10 | 228 | 2 J | PASS | Low | < | Low | No | Low | No | Yes | Yes | Yes | 8 | 4 |
| Method 5 | 44 | B | PASS | Low | | | | Moderate | Yes | Yes | Yes | | 8 | 4 |
| Method 3 | 21 | 3 | PASS | Moderate | > | Low | No | | | | Yes | Yes | 8 | 4 |
| Method 7 | 100 | 3 D | PASS | Moderate | > | Low | No | Low | Yes | Yes | Yes | Yes | 8 | 4 |
| Method 9 | 189 | 3 E | PASS | Moderate | ,< | Low | No | Moderate | Yes | Yes | Yes | Yes | 8 | 4 |
| Method 4 | 35 | 5 | PASS | Moderate | < | Moderate | No | | | | Yes | No | 8 | 4 |
| Method 7 | 105 | 4 E | PASS | Moderate | > | Moderate | Yes | Moderate | Yes | Yes | Yes | Yes | 8 | 4 |
| Method 7 | 108 | 5 D | PASS | Moderate | > | Moderate | No | Low | Yes | Yes | Yes | No | 8 | 4 |
| Method 9 | 197 | 5 E | PASS | Moderate | ,< | Moderate | No | Moderate | Yes | Yes | Yes | No | 8 | 4 |
| Method 10 | 236 | 4 M | PASS | Moderate | < | Moderate | Yes | Low | No | Yes | Yes | Yes | 8 | 4 |
| Method 4 | 36 | 6 | PASS | Moderate | < | High | Yes | | | | Yes | Yes | 8 | 4 |
| Method 9 | 200 | 6 G | PASS | Moderate | < | High | Yes | Low | Yes | No | Yes | Yes | 8 | 4 |
| Method 5 | 47 | D | PASS | Moderate | | | | Low | Yes | Yes | Yes | | 8 | 4 |
| Method 5 | 48 | E | PASS | Moderate | | | | Moderate | Yes | Yes | Yes | | 8 | 4 |
| Method 9 | 208 | 8 D | PASS | High | < | Moderate | Yes | Low | Yes | Yes | Yes | Yes | 8 | 4 |
| Method 8 | 137 | 1 K | PASS | Low | > | Low | Yes | Moderate | No | Yes | Yes | Yes | 7 | 3 |
| Method 8 | 140 | 2 J | PASS | Low | > | Low | No | Low | No | Yes | Yes | Yes | 7 | 3 |
| Method 10 | 229 | 2 K | PASS | Low | < | Low | No | Moderate | No | Yes | Yes | Yes | 7 | 3 |
| Method 6 | 55 | J | PASS | Low | | | | Low | No | Yes | Yes | | 7 | 3 |
| Method 7 | 101 | 3 E | PASS | Moderate | > | Low | No | Moderate | Yes | Yes | Yes | Yes | 7 | 3 |
| Method 10 | 232 | 3 M | PASS | Moderate | < | Low | No | Low | No | Yes | Yes | Yes | 7 | 3 |
| Method 3 | 23 | 5 | PASS | Moderate | > | Moderate | No | | | | Yes | No | 7 | 3 |
| Method 7 | 109 | 5 E | PASS | Moderate | > | Moderate | No | Moderate | Yes | Yes | Yes | No | 7 | 3 |
| Method 8 | 148 | 4 M | PASS | Moderate | > | Moderate | Yes | Low | No | Yes | Yes | Yes | 7 | 3 |
| Method 10 | 237 | 4 N | PASS | Moderate | < | Moderate | Yes | Moderate | No | Yes | Yes | Yes | 7 | 3 |
| Method 10 | 240 | 5 M | PASS | Moderate | < | Moderate | No | Low | No | Yes | Yes | No | 7 | 3 |
| Method 3 | 24 | 6 | PASS | Moderate | > | High | Yes | | | | Yes | Yes | 7 | 3 |
| Method 7 | 112 | 6 G | PASS | Moderate | > | High | Yes | Low | Yes | No | Yes | Yes | 7 | 3 |
| Method 9 | 201 | 6 H | PASS | Moderate | < | High | Yes | Moderate | Yes | No | Yes | Yes | 7 | 3 |
| Method 9 | 204 | 7 G | PASS | Moderate | < | High | No | Low | Yes | No | Yes | No | 7 | 3 |
| Method 7 | 120 | 8 D | PASS | High | > | Moderate | Yes | Low | Yes | Yes | Yes | Yes | 7 | 3 |
| Method 9 | 209 | 8 E | PASS | High | < | Moderate | Yes | Moderate | Yes | Yes | Yes | Yes | 7 | 3 |
| Method 9 | 212 | 9 D | PASS | High | < | Moderate | No | Low | Yes | No | Yes | No | 7 | 3 |
| Method 9 | 216 | 10 G | PASS | High | < | High | Yes | Low | Yes | Yes | Yes | Yes | 7 | 3 |
| Method 5 | 51 | G | PASS | High | | | | Low | Yes | Yes | Yes | | 7 | 3 |
| Method 8 | 141 | 2 K | PASS | Low | > | Low | No | Moderate | No | Yes | Yes | Yes | 6 | 3 |
| Method 9 | 182 | 1 C | PASS | Low | < | Low | Yes | High | Yes | Yes | Yes | Yes | 6 | 3 |
| Method 6 | 56 | K | PASS | Low | | | | Moderate | No | Yes | Yes | | 6 | 3 |
| Method 5a | 67 | A | PASS | Low | | | | Low | Yes | No | Yes | | 6 | 3 |
| Method 8 | 144 | 3 M | PASS | Moderate | > | Low | No | Low | No | Yes | Yes | Yes | 6 | 3 |
| Method 10 | 233 | 3 N | PASS | Moderate | ,< | Low | No | Moderate | No | Yes | Yes | Yes | 6 | 3 |
| Method 8 | 149 | 4 N | PASS | Moderate | > | Moderate | Yes | Moderate | No | Yes | Yes | Yes | 6 | 3 |
| Method 8 | 152 | 5 M | PASS | Moderate | > | Moderate | No | Low | No | Yes | Yes | No | 6 | 3 |
| Method 10 | 241 | 5 N | PASS | Moderate | ,< | Moderate | No | Moderate | No | Yes | Yes | No | 6 | 3 |
| Method 7 | 113 | 6 H | PASS | Moderate | > | High | Yes | Moderate | Yes | No | Yes | Yes | 6 | 3 |
| Method 7 | 116 | 7 G | PASS | Moderate | > | High | No | Low | Yes | No | Yes | No | 6 | 3 |
| Method 9 | 205 | 7 E | PASS | Moderate | ,< | High | No | Moderate | Yes | No | Yes | No | 6 | 3 |
| Method 10 | 244 | 6 P | PASS | Moderate | < | High | Yes | Low | No | No | Yes | Yes | 6 | 3 |
| Method 6 | 59 | M | PASS | Moderate | | | | Low | No | Yes | Yes | | 6 | 3 |
| Method 6 | 60 | N | PASS | Moderate | | | | Moderate | No | Yes | Yes | | 6 | 3 |
| Method 4 | 38 | 8 | PASS | High | < | Moderate | Yes | | | | Yes | Yes | 6 | 3 |
| Method 7 | 121 | 8 E | PASS | High | > | Moderate | Yes | Moderate | Yes | Yes | Yes | Yes | 6 | 3 |
| Method 7 | 124 | 9 D | PASS | High | > | Moderate | No | Low | Yes | No | Yes | No | 6 | 3 |
| Method 9 | 213 | 9 E | PASS | High | ,< | Moderate | No | Moderate | Yes | No | Yes | No | 6 | 3 |
| Method 10 | 252 | 8 M | PASS | High | < | Moderate | Yes | Low | No | Yes | Yes | Yes | 6 | 3 |
| Method 4 | 40 | 10 | PASS | High | < | High | Yes | | | | Yes | Yes | 6 | 3 |
| Method 7 | 128 | 10 G | PASS | High | > | High | Yes | Low | Yes | Yes | Yes | Yes | 6 | 3 |
| Method 9 | 217 | 10 H | PASS | High | < | High | Yes | Moderate | Yes | Yes | Yes | Yes | 6 | 3 |
| Method 9 | 220 | 11 G | PASS | High | < | High | No | Low | Yes | Yes | Yes | No | 6 | 3 |
| | 94 | 1 C | PASS | Low | > | Low | Yes | High | Yes | Yes | Yes | Yes | 5 | 2 |
| Method 9 | 186 | 2 C | PASS | Low | ,< | Low | No | High | Yes | Yes | Yes | Yes | 5 | 2 |
| Method 1 | 5 | | PASS | Low | | | | | | | Yes | | 5 | 2 |
| Method 5 | 45 | C | PASS | Low | | | | High | Yes | Yes | Yes | | 5 | 2 |
| Method 5a | 68 | B | PASS | Low | | | | Moderate | Yes | No | Yes | | 5 | 2 |
| Method 8 | 145 | 3 N | PASS | Moderate | > | Low | No | Moderate | No | Yes | Yes | Yes | 5 | 2 |
| Method 8 | 153 | 5 N | PASS | Moderate | > | Moderate | No | Moderate | No | Yes | Yes | No | 5 | 2 |

TABLE 14-continued

| Method | 1 | Meth-od | Leak Detection Method | UT Local Measurement Corrosion Rate | | API 653 Tank Floor Thickness Corrosion Rate | UT Local Correlated with API 653 Corrosion Rate | AE Corrosion Activity | UT Local Correlated with AE Corrosion | AE Correlated Leak Detection | UT Min Thickness >0.1, 0.05 in. Over ETI | API 653 Min Thickness >0.1, 0.05 in. Over ETI | Overall Confidence of Integrity Assessment | Extension Time Interval (Years) UT > OOSI &/OR AE PASS |
|---|---|---|---|---|---|---|---|---|---|---|---|---|---|---|
| Method 9 | 194 | 4 F | PASS | Moderate | ,< | Moderate | Yes | High | Yes | Yes | Yes | Yes | 5 | 2 |
| Method 7 | 117 | 7 E | PASS | Moderate | > | High | No | Moderate | Yes | No | Yes | No | 5 | 2 |
| Method 8 | 156 | 6 P | PASS | Moderate | > | High | Yes | Low | No | No | Yes | Yes | 5 | 2 |
| Method 10 | 245 | 6 Q | PASS | Moderate | < | High | Yes | Moderate | No | No | Yes | Yes | 5 | 2 |
| Method 10 | 248 | 7 P | PASS | Moderate | < | High | No | Low | No | No | Yes | No | 5 | 2 |
| Method 5 | 49 | F | PASS | Moderate | | | | High | Yes | Yes | Yes | | 5 | 2 |
| Method 5a | 71 | D | PASS | Moderate | | | | Low | Yes | No | Yes | | 5 | 2 |
| Method 5a | 72 | E | PASS | Moderate | | | | Moderate | Yes | No | Yes | | 5 | 2 |
| Method 3 | 26 | 8 | PASS | High | > | Moderate | Yes | | | | Yes | Yes | 5 | 2 |
| Method 7 | 125 | 9 E | PASS | High | > | Moderate | No | Moderate | Yes | No | Yes | No | 5 | 2 |
| Method 8 | 164 | 8 M | PASS | High | > | Moderate | Yes | Low | No | Yes | Yes | Yes | 5 | 2 |
| Method 10 | 253 | 8 N | PASS | High | < | Moderate | Yes | Moderate | No | Yes | Yes | Yes | 5 | 2 |
| Method 10 | 256 | 9 M | PASS | High | < | Moderate | No | Low | No | No | Yes | No | 5 | 2 |
| Method 3 | 28 | 10 | PASS | High | > | High | Yes | | | | Yes | Yes | 5 | 2 |
| Method 7 | 129 | 10 H | PASS | High | > | High | Yes | Moderate | Yes | Yes | Yes | Yes | 5 | 2 |
| Method 7 | 132 | 11 G | PASS | High | > | High | No | Low | Yes | Yes | Yes | No | 5 | 2 |
| Method 9 | 221 | 11 H | PASS | High | ,< | High | No | Moderate | Yes | Yes | Yes | No | 5 | 2 |
| Method 10 | 260 | 10 P | PASS | High | < | High | Yes | Low | No | Yes | Yes | Yes | 5 | 2 |
| Method 5 | 52 | H | PASS | High | | | | Moderate | Yes | Yes | Yes | | 5 | 2 |
| Method 6 | 63 | P | PASS | High | | | | Low | No | Yes | Yes | | 5 | 2 |
| Method 2 | 12 | 1 | PASS | | | Low | | | | | | Yes | 5 | 2 |
| Method 7 | 98 | 2 C | PASS | Low | > | Low | No | High | Yes | Yes | Yes | Yes | 4 | 2 |
| Method 10 | 226 | 1 L | PASS | Low | < | Low | Yes | High | No | Yes | Yes | Yes | 4 | 2 |
| Method 6a | 79 | J | PASS | Low | | | | Low | No | No | Yes | | 4 | 2 |
| Method 9 | 190 | 3 F | PASS | Moderate | < | Low | No | High | Yes | Yes | Yes | Yes | 4 | 2 |
| Method 7 | 106 | 4 F | PASS | Moderate | > | Moderate | Yes | High | Yes | Yes | Yes | Yes | 4 | 2 |
| Method 9 | 198 | 5 F | PASS | Moderate | < | Moderate | No | High | Yes | Yes | Yes | No | 4 | 2 |
| Method 8 | 157 | 6 O | PASS | Moderate | > | High | Yes | Moderate | No | No | Yes | Yes | 4 | 2 |
| Method 8 | 160 | 7 P | PASS | Moderate | > | High | No | Low | No | No | Yes | No | 4 | 2 |
| Method 10 | 249 | 7 O | PASS | Moderate | ,< | High | No | Moderate | No | No | Yes | No | 4 | 2 |
| Method 1 | 7 | | PASS | Moderate | | | | | | | Yes | | 4 | 2 |
| Method 8 | 165 | 8 N | PASS | High | > | Moderate | Yes | Moderate | No | Yes | Yes | Yes | 4 | 2 |
| Method 8 | 168 | 9 M | PASS | High | > | Moderate | No | Low | No | No | Yes | No | 4 | 2 |
| Method 10 | 257 | 9 N | PASS | High | ,< | Moderate | No | Moderate | No | No | Yes | No | 4 | 2 |
| Method 7 | 133 | 11 H | PASS | High | > | High | No | Moderate | Yes | Yes | Yes | No | 4 | 2 |
| Method 8 | 172 | 10 P | PASS | High | > | High | Yes | Low | No | Yes | Yes | Yes | 4 | 2 |
| Method 10 | 261 | 10 O | PASS | High | < | High | Yes | Moderate | No | Yes | Yes | Yes | 4 | 2 |
| Method 10 | 264 | 11 P | PASS | High | < | High | No | Low | No | Yes | Yes | No | 4 | 2 |
| Method 1 | 9 | | PASS | High | | | | | | | Yes | | 4 | 2 |
| Method 5a | 75 | G | PASS | High | | | | Low | Yes | No | Yes | | 4 | 2 |
| Method 2 | 14 | 3 | PASS | | | Moderate | | | | | | Yes | 4 | 2 |
| Method 8 | 138 | 1 L | PASS | Low | > | Low | Yes | High | No | Yes | Yes | Yes | 3 | 2 |
| Method 10 | 230 | 2 L | PASS | Low | ,< | Low | No | High | No | Yes | Yes | Yes | 3 | 2 |
| Method 6 | 57 | L | PASS | Low | | | | High | No | Yes | Yes | | 3 | 2 |
| Method 6a | 80 | K | PASS | Low | | | | Moderate | No | No | Yes | | 3 | 2 |
| Method 7 | 102 | 3 F | PASS | Moderate | > | Low | No | High | Yes | Yes | Yes | Yes | 3 | 2 |
| Method 7 | 110 | 5 F | PASS | Moderate | > | Moderate | No | High | Yes | Yes | Yes | No | 3 | 2 |
| Method 10 | 238 | 4 O | PASS | Moderate | ,< | Moderate | Yes | High | No | Yes | Yes | Yes | 3 | 2 |
| Method 4 | 37 | 7 | PASS | Moderate | ,< | High | No | | | | Yes | No | 3 | 2 |
| Method 8 | 161 | 7 O | PASS | Moderate | > | High | No | Moderate | No | No | Yes | No | 3 | 2 |
| Method 9 | 202 | 6 F | PASS | Moderate | ,< | High | Yes | High | Yes | No | Yes | Yes | 3 | 2 |
| Method 6 | 61 | O | PASS | Moderate | | | | High | No | Yes | Yes | | 3 | 2 |
| Method 6a | 83 | M | PASS | Moderate | | | | Low | No | No | Yes | | 3 | 2 |
| Method 6a | 84 | N | PASS | Moderate | | | | Moderate | No | No | Yes | | 3 | 2 |
| Method 4 | 99 | 9 | PASS | High | < | Moderate | No | | | | Yes | No | 3 | 2 |
| Method 8 | 169 | 9 N | PASS | High | > | Moderate | No | Moderate | No | No | Yes | No | 3 | 2 |
| Method 9 | 210 | 8 F | PASS | High | ,< | Moderate | Yes | High | Yes | Yes | Yes | Yes | 3 | 2 |
| Method 8 | 173 | 10 O | PASS | High | > | High | Yes | Moderate | No | Yes | Yes | Yes | 3 | 2 |
| Method 8 | 176 | 11 P | PASS | High | > | High | No | Low | No | Yes | Yes | No | 3 | 2 |
| Method 10 | 265 | 11 O | PASS | High | ,< | High | No | Moderate | No | Yes | Yes | No | 3 | 2 |
| Method 6 | 64 | O | PASS | High | | | | Moderate | No | Yes | Yes | | 3 | 2 |
| Method 2 | 16 | 5 | PASS | | | High | | | | | | Yes | 3 | 2 |
| Method 8 | 142 | 2 L | PASS | Low | > | Low | No | High | No | Yes | Yes | Yes | 2 | 1 |
| Method 5a | 69 | C | PASS | Low | | | | High | Yes | No | Yes | | 2 | 1 |
| Method 10 | 234 | 3 O | PASS | Moderate | < | Low | No | High | No | Yes | Yes | Yes | 2 | 1 |
| Method 8 | 150 | 4 O | PASS | Moderate | > | Moderate | Yes | High | No | Yes | Yes | Yes | 2 | 1 |
| Method 10 | 242 | 5 O | PASS | Moderate | < | Moderate | No | High | No | Yes | Yes | No | 2 | 1 |
| Method 3 | 25 | 7 | PASS | Moderate | > | High | No | | | | Yes | No | 2 | 1 |
| Method 7 | 114 | 6 F | PASS | Moderate | > | High | Yes | High | Yes | No | Yes | Yes | 2 | 1 |
| Method 9 | 206 | 7 F | PASS | Moderate | < | High | No | High | Yes | No | Yes | No | 2 | 1 |
| Method 5a | 73 | F | PASS | Moderate | | | | High | Yes | No | Yes | | 2 | 1 |
| Method 3 | 27 | 9 | PASS | High | > | Moderate | No | | | | Yes | No | 2 | 1 |

TABLE 14-continued

| Method | 1 | Leak Detection Method | UT Local Measurement Method | API 653 Tank Floor Thickness Corrosion Rate | | UT Local Correlated with API 653 Corrosion Rate | AE Corrosion Activity | UT Local Correlated with AE Corrosion | AE Correlated Leak Detection | UT Min Thickness >0.1, 0.05 in. Over ETI | API 653 Min Thickness >0.1, 0.05 in. Over ETI | Overall Confidence of Integrity Assessment | Extension Time Interval (Years) UT > OOSI &/OR AE PASS |
|---|---|---|---|---|---|---|---|---|---|---|---|---|---|
| Method 7 | 122 | 8 F | PASS | High | > | Moderate | Yes | High | Yes | Yes | Yes | Yes | 2 | 1 |
| Method 9 | 214 | 9 F | PASS | High | < | Moderate | No | High | Yes | No | Yes | No | 2 | 1 |
| Method 4 | 41 | 11 | PASS | High | < | High | No | | | | Yes | No | 2 | 1 |
| Method 8 | 177 | 11 O | PASS | High | > | High | No | Moderate | No | Yes | Yes | No | 2 | 1 |
| Method 9 | 218 | 10 I | PASS | High | ,< | High | Yes | High | Yes | Yes | Yes | Yes | 2 | 1 |
| Method 5 | 53 | I | PASS | High | | | | High | Yes | Yes | Yes | | 2 | 1 |
| Method 5a | 76 | H | PASS | High | | | | Moderate | Yes | No | Yes | | 2 | 1 |
| Method 6a | 87 | P | PASS | High | | | | Low | No | No | Yes | | 2 | 1 |
| Method 0 | 2 | | PASS | | | | | | | | | | 2 | 1 |
| Method 8 | 146 | 3 O | PASS | Moderate | > | Low | No | High | No | Yes | Yes | Yes | 1 | 0 |
| Method 8 | 154 | 5 O | PASS | Moderate | > | Moderate | No | High | No | Yes | Yes | No | 1 | 0 |
| Method 7 | 118 | 7 F | PASS | Moderate | > | High | No | High | Yes | No | Yes | No | 1 | 0 |
| Method 10 | 246 | 6 R | PASS | Moderate | ,< | High | Yes | High | No | No | Yes | Yes | 1 | 0 |
| Method 10 | 250 | 7 R | PASS | Moderate | > | High | No | High | No | No | Yes | No | 1 | 0 |
| Method 7 | 126 | 9 F | PASS | High | > | Moderate | No | High | Yes | No | Yes | No | 1 | 0 |
| Method 10 | 254 | 8 O | PASS | High | ,< | Moderate | Yes | High | No | Yes | Yes | Yes | 1 | 0 |
| Method 10 | 258 | 9 O | PASS | High | < | Moderate | No | High | No | No | Yes | No | 1 | 0 |
| Method 3 | 29 | 11 | PASS | High | > | High | No | | | | Yes | No | 1 | 0 |
| Method 7 | 130 | 10 I | PASS | High | > | High | Yes | High | Yes | Yes | Yes | Yes | 1 | 0 |
| Method 9 | 222 | 11 I | PASS | High | < | High | No | High | Yes | Yes | Yes | No | 1 | 0 |
| Method 10 | 262 | 10 R | PASS | High | ,< | High | Yes | High | No | Yes | Yes | Yes | 1 | 0 |
| Method 10 | 266 | 11 R | PASS | High | < | High | No | High | No | Yes | Yes | No | 1 | 0 |
| Method 1 | 6 | | PASS | Low | | | | | | | No | | 0 | 0 |
| Method 6a | 81 | L | PASS | Low | | | | High | No | No | Yes | | 0 | 0 |
| Method 8 | 158 | 6 R | PASS | Moderate | > | High | Yes | High | No | No | Yes | Yes | 0 | 0 |
| Method 8 | 162 | 7 R | PASS | Moderate | > | High | No | High | No | No | Yes | No | 0 | 0 |
| Method 1 | 8 | | PASS | Moderate | | | | | | | No | | 0 | 0 |
| Method 6a | 85 | O | PASS | Moderate | | | | High | No | No | Yes | | 0 | 0 |
| Method 8 | 166 | 8 O | PASS | High | > | Moderate | Yes | High | No | Yes | Yes | Yes | 0 | 0 |
| Method 8 | 170 | 9 O | PASS | High | > | Moderate | No | High | No | No | Yes | No | 0 | 0 |
| Method 7 | 134 | 11 I | PASS | High | > | High | No | High | Yes | Yes | Yes | No | 0 | 0 |
| Method 8 | 174 | 10 R | PASS | High | > | High | Yes | High | No | Yes | Yes | Yes | 0 | 0 |

While certain representative embodiments and details have been shown for purposes of illustrating the invention, it will be apparent to those skilled in the art that various changes in the methods and apparatus disclosed herein may be made without departing from the scope of the invention which is defined in the appended claims.

What is claimed is:

1. A method for determining the integrity of a storage tank comprising the steps of:
   (a) performing a leak detection test;
   (b) estimating the thickness of the tank floor in at least one location of the tank; and
   (c) conducting a risk assessment using statistical data of tank failures including data related to tank corrosion conditions, thereby assessing the probability of structural failure or leaking of the tank within a selected time period.

2. The method of claim 1, wherein the thickness of the tank floor over at least one region of the tank is measured and used to estimate the corrosion rate and the thickness of the tank floor as a function of the selected time period to determine if a minimum floor thickness can be maintained during said period.

3. The method of claim 2, wherein said corrosion rate is computed using said floor thickness, a previous measurement of floor thickness, and the time between said thickness measurements.

4. The method of claim 3, wherein said previous measurement of floor thickness is the original floor thickness of the tank.

5. The method of claim 3, wherein said previous measurement of floor thickness is obtained from a floor thickness measurement made during an out-of-tank inspection.

6. The method of claim 3, wherein said previous measurement of floor thickness is obtained from a floor thickness measurement made during an in-tank inspection.

7. The method of claim 2, wherein said thickness measurement is made at one region of said tank floor and used to estimate the minimum thickness of the entire floor using the minimum thickness of said local thickness measurement.

8. The method of claim 2, wherein said thickness measurement is made at one region of said tank floor and used to estimate the minimum thickness of the entire floor using a multiple of the standard deviation of said floor thickness measurements at said region.

9. The method of claim 2, wherein said thickness measurement is made at one region of said tank floor and used to estimate the minimum thickness of the entire floor using the difference between the mean or median thickness measurement and the minimum floor thickness measurement at said region.

10. The method of claim 2, wherein a previous out-of-service inspection of the tank floor thickness is used to estimate the minimum thickness and maximum corrosion rate from said in-tank floor thickness measurements.

11. The method of claim 10, wherein said in-tank measurement is referenced to previous floor thickness measurements made during said previous out-of-service inspection in the same region as said in-tank thickness measurements and used with said previous out-of-tank inspection of said tank floor to estimate the floor thickness and corrosion rate at another location on said tank floor.

12. The method of claim 11, wherein said minimum floor thickness is computed.

13. The method of claim 11, wherein said maximum corrosion rate of said floor is computed.

14. The method of claim 11, wherein the percentage increase in said in-tank measurements over those measured in said previous out-of-service tank floor inspection is used to compute the percentage increase of all other previous measurements of said tank floor from said out-of-service tank floor inspection.

15. The method of claim 14, wherein said corrosion rate for all previous thickness measurements made during said previous out-of-service inspection is computed over the time interval between said in-tank measurements of floor thickness and said out-of-service measurements of said floor thickness.

16. The method of claim 15, wherein said corrosion rates are used to determine the maximum corrosion rate in said tank.

17. The method of claim 11, wherein the maximum of the relative percentage in said in-tank measurements over those measured in said previous out-of-service tank floor inspection or the percentage increase said previous out-of-service inspection of floor thickness and a previous out-of-tank inspection of floor thickness or the original tank floor thickness is used to compute the percentage increase of all other previous measurements of said tank floor from said out-of-service tank floor inspection.

18. The method of claim 17, wherein said corrosion rate for all previous thickness measurements made during said previous out-of-service inspection is computed over the time interval between said in-tank measurements of floor thickness and said out-of-service measurements of said floor thickness.

19. The method of claim 18, wherein said corrosion rates are used to determine the maximum corrosion rate in said tank.

20. The method of claim 2, wherein the results of an acoustic emission (AE) inspection of said tank floor for active corrosion is used to determine whether or not the thickness measurements of the tank floor in one vicinity of said tank floor can be used to estimate the thickness and corrosion rate of another location in said tank floor.

21. The method of claim 20, wherein said external leak detection method uses at least one acoustic sensor mounted on an external wall of an aboveground storage tank to detect the acoustic signal being generated by a leak.

22. The method of claim 21, wherein three or more acoustic sensors are used.

23. The method of claim 22, wherein at least one of said acoustic sensors is at a different vertical elevation.

24. The method of claim 20, wherein said external leak detection method uses at least one acoustic sensor mounted in the fluid inside said storage tank to detect the acoustic signal being generated by a leak in said tank floor or tank walls.

25. The method of claim 24, wherein a multiplicity of acoustic sensors are used.

26. The method of claim 24, wherein at least one of said acoustic sensors is at a different vertical elevation.

27. The method of claim 24, wherein at least three acoustic sensors are used.

28. The method of claim 27, wherein at least one of said acoustic sensors is at a different vertical elevation.

29. The method of claim 27, wherein the horizontal plane formed by the location of at least three acoustic sensors is not perpendicular to said tank floor.

30. The method of claim 2, where the results of an acoustic emission (AE) inspection of said tank floor for active corrosion is used with previous out-of-service tank inspections of floor thicknesses and corrosion rates to determine whether the thickness measurements of the tank floor in one vicinity of said tank floor can be used to estimate the thickness and corrosion rate of another location in said tank floor.

31. The method of claim 2, where the results of an acoustic emission (AE) inspection of said tank floor for active corrosion is used with previous in-tank inspections of floor thicknesses and corrosion rates to determine whether or not the thickness measurements of the tank floor in any one vicinity of said tank floor can be used to estimate the thickness and corrosion rate of another location in said tank floor.

32. The method of claim 31, wherein said internal leak detection method measures the output of the test as a volume change or a volume rate.

33. The method of claim 31, wherein said internal leak detection method is a volumetric method using a level gauge and one or more arrays of one or more temperature sensors extending over the depth of the tank.

34. The method of claim 31, wherein said internal leak detection method is a mass-based method.

35. The method of claim 34, wherein said mass-based leak detection method uses a differential pressure sensor that measures the difference in level between the liquid in a tube, which is allowed to fill to the tank level and is then closed, and the level of the liquid in the tank.

36. The method of claim 35, wherein said differential pressure sensor is located at the bottom of the tank in a sealed container.

37. The method of claim 35, wherein said differential pressure sensor is located at a location outside said tank.

38. The method of claim 34, wherein said mass-based leak detection method uses a differential pressure sensor that measures the difference in level between the liquid in the tank and a reference pressure.

39. The method of claim 2, wherein said AE measurements are used to categorize the condition of the floor of the tank in terms of no active corrosion, some active corrosion, active corrosion, moderate corrosion, or severe corrosion.

40. The method of claim 1, wherein the results of an acoustic emission (AE) inspection of said tank floor for active corrosion is used to determine the magnitude of said corrosion in the tank floor.

41. The method of claim 1, wherein the leak detection method is an internal leak detection method that measures the output of the test in volumetric units.

42. The method of claim 1, wherein the leak detection method is an external leak detection method.

43. The method of claim 42, wherein said external leak detection method uses a tracer that is inserted into the liquid in the tank and is sensed outside the tank.

44. The method of claim 42, wherein said external leak detection method uses one or more constituents of the liquid in the tank as a tracer, which is sensed outside the tank.

45. The method of claim 42, wherein said external leak detection method senses the accumulation of the liquid in a containment space such as a secondary containment space or the interstitial space of a double bottom tank.

46. The method of claim 42, wherein said external leak detection method uses external sensors to detect the presence of the tank fluid in the backfill or a secondary containment system.

47. The method of claim 42, wherein said external leak detection method uses at least one acoustic sensor mounted on the external wall of said aboveground storage tank to detect the acoustic signal being generated by a leak in the tank floor or the tank walls.

48. The method of 47, wherein at least one of said acoustic sensors is at a different vertical elevation.

49. The method of claim 47, wherein three or more acoustic sensors are used.

50. The method of claim 42, wherein said external leak detection method uses at least one acoustic sensor mounted in the fluid inside said storage tank, to defect the acoustic signal being generated by a leak in said tank floor or tank walls.

51. The method of claim 50, wherein three or more acoustic sensors are used.

52. The method of claim 51, wherein at least one of said acoustic sensors is at a different vertical elevation.

53. The method of claim 51, wherein the horizontal plane formed by the locations of at least three of said acoustic sensors is not perpendicular or parallel to said tank floor.

54. The method of claim 1, further comprising the step of determining an extension time interval is also based on the cost consequences derived from said probability.

55. The method of claim 1, wherein a Bayesian inspection of a tank is performed comprised of a leak detection test.

56. The method of claim 55, wherein said tank passes said leak detection test.

57. The method of claim 55, wherein said Bayesian inspection is also comprised of one or more in-tank measurement of floor thickness.

58. The method of claim 57, wherein said in-tank floor thickness measurements are used to estimate the minimum thickness of said tank floor at any location in the tank floor.

59. The method of claim 57, wherein said in-tank floor thickness measurements are used to estimate the maximum corrosion rate of said tank floor at any location in the tank floor.

60. The method of claim 59, wherein said in-tank floor thickness measurements are used to estimate the maximum corrosion rate of said tank floor at any location in the tank floor.

61. The method of claim 55, wherein said Bayesian inspection is also comprised of previous out-of-service, internal inspections.

62. The method of claim 61, wherein said in-tank floor thickness measurements are used to estimate the minimum thickness of said tank floor at any location in said tank.

63. The method of claim 55, wherein said Bayesian inspection is also comprised of an acoustic emission (AE) measurement of tank floor corrosion activity at any location is said tank floor.

64. The method of claim 63, wherein said Bayesian inspection is also comprised of a previous out-of-service, internal inspection of said tank floor.

65. The method of 64, wherein said Bayesian inspection is also comprised of an acoustic emission (AE) measurement of tank floor corrosion activity.

* * * * *